United States Patent [19]
Hoffman

[11] Patent Number: 5,517,700
[45] Date of Patent: May 21, 1996

[54] GOGGLE AND DESICCANT ASSEMBLY

[75] Inventor: Ned Hoffman, Berkeley, Calif.

[73] Assignee: Sports-Mitt International, Berkeley, Calif.

[21] Appl. No.: 118,053

[22] Filed: Sep. 8, 1993

[51] Int. Cl.$^6$ ............................................ A61F 9/02
[52] U.S. Cl. .................................. 2/428; 2/435
[58] Field of Search .................. 2/435, 436, 426, 2/9, 424, 425, 428, 430; 351/62

[56] References Cited

U.S. PATENT DOCUMENTS

| | | | |
|---|---|---|---|
| 1,562,350 | 11/1925 | Luckey | 2/435 X |
| 2,280,055 | 4/1942 | Andersen | 2/435 |
| 4,414,693 | 11/1983 | Brody | 2/435 |

*Primary Examiner*—Peter Nerbun
*Attorney, Agent, or Firm*—Ali Kamarei

[57] ABSTRACT

A non-fogging athletic goggle or mask assembly, comprising an athletic goggle or mask in combination with a desiccant assembly, is disclosed. According to one embodiment, an athletic mask or goggle is provided with at least one desiccant chamber formed in a portion of the mask or goggle so as not to obstruct vision. The desiccant chamber includes a gate that can be deployed or retracted to close off or expose the interior of desiccant chamber. The desiccant chamber is provided with a tablet or pre-packaged desiccant, which is retained within the desiccant chamber during use of the goggle or mask and can be replaced upon saturation. When the mask is worn, water vapor in the air trapped by the goggle or mask is absorbed by the desiccant, thereby preventing fogging of the goggle or mask. The desiccant capsule or the desiccant chamber may be further provided with a water vapor permeable membrane that allows water vapor to pass but excludes liquid water. The desiccant material may be combined with an indicator substance that changes color as the desiccant becomes saturated with water.

6 Claims, 22 Drawing Sheets

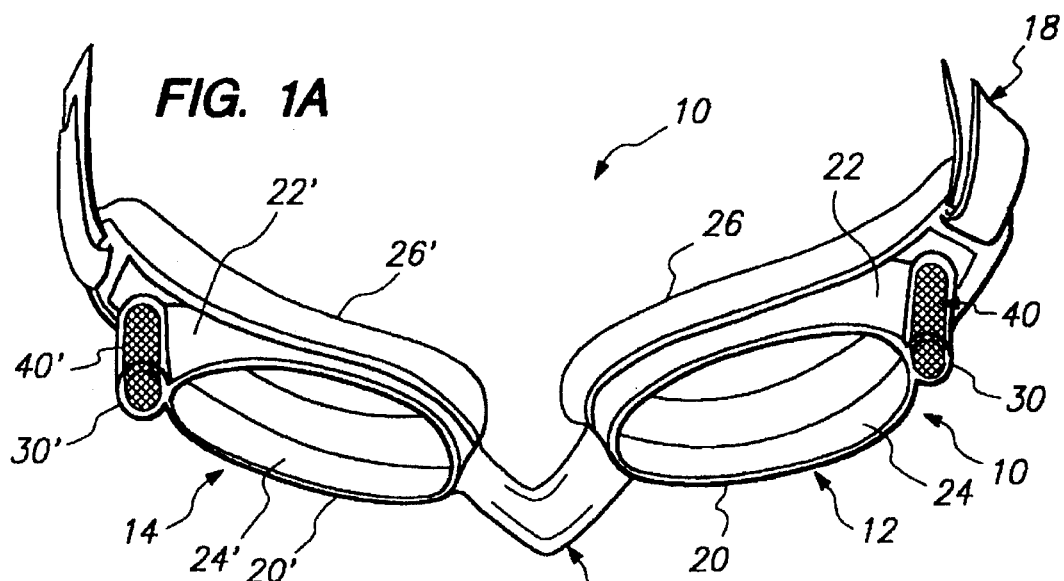
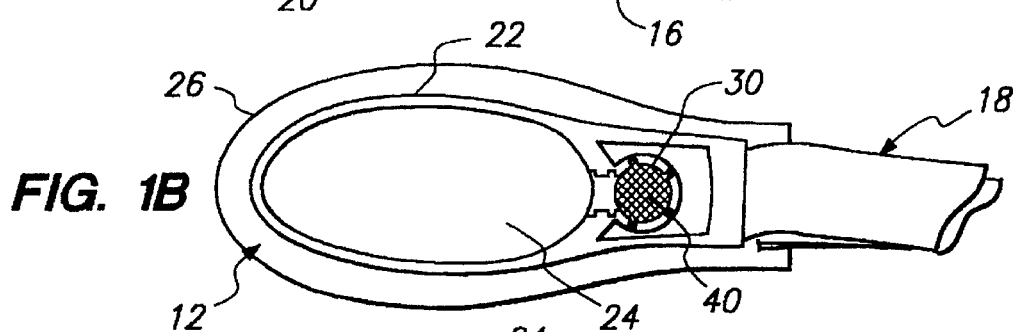
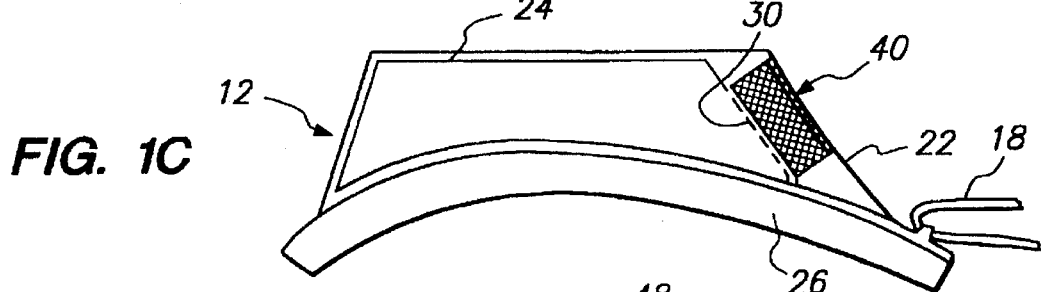
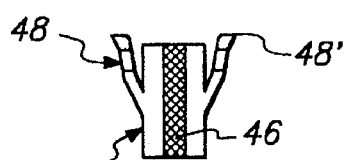
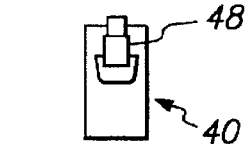
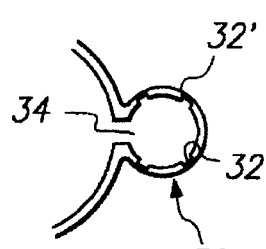
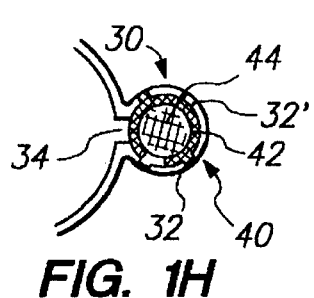
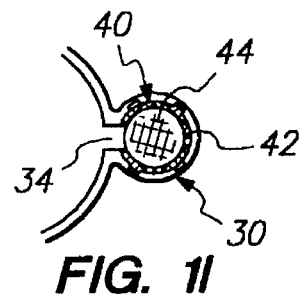

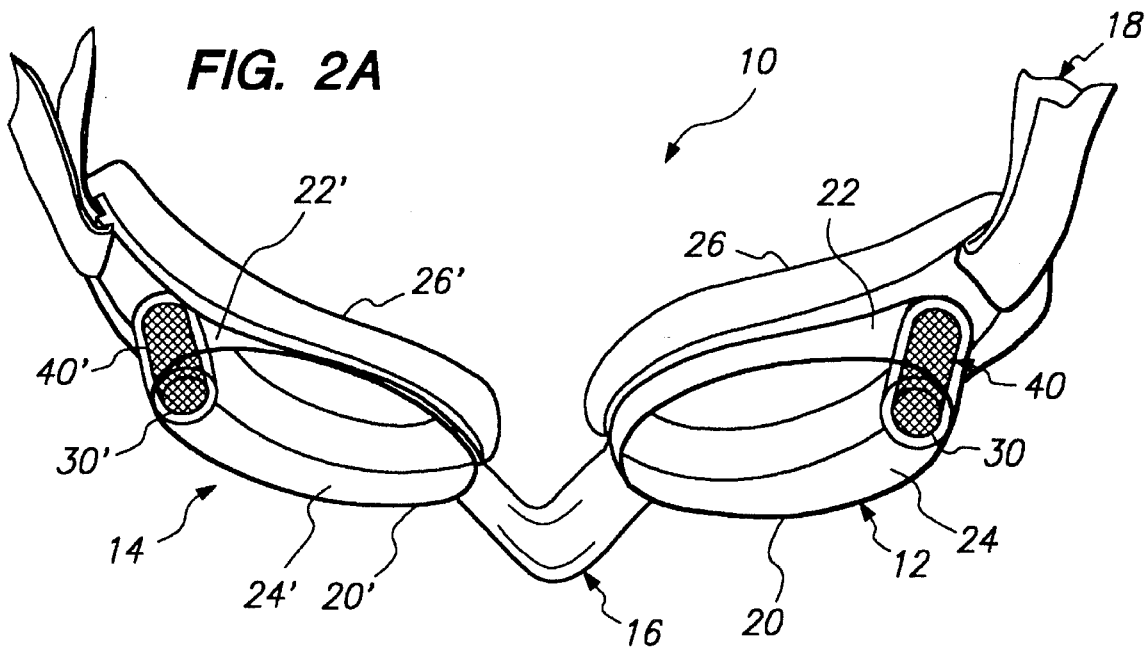
FIG. 2A
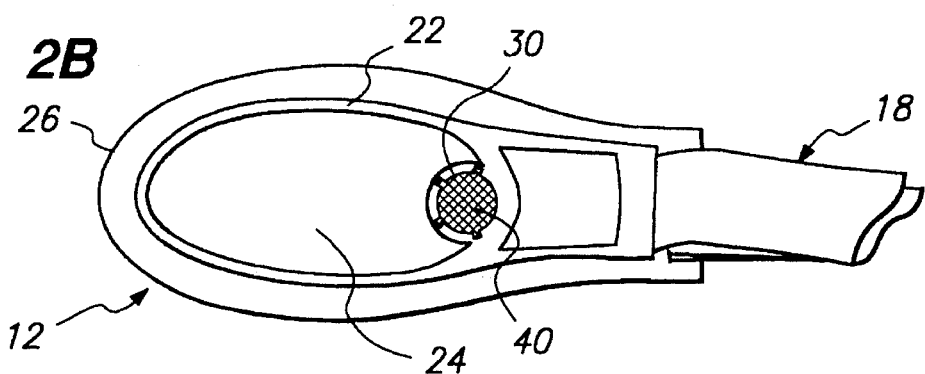
FIG. 2B
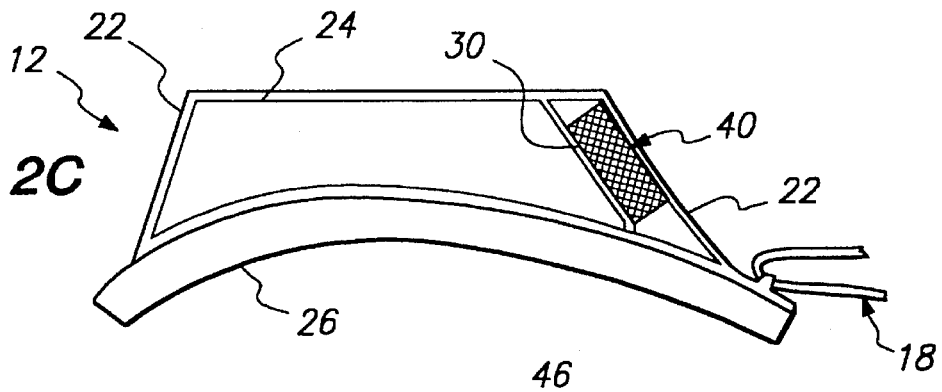
FIG. 2C
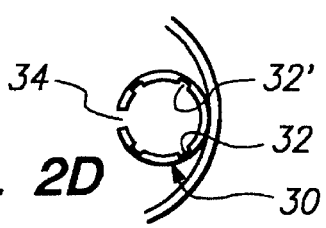
FIG. 2D
FIG. 2E

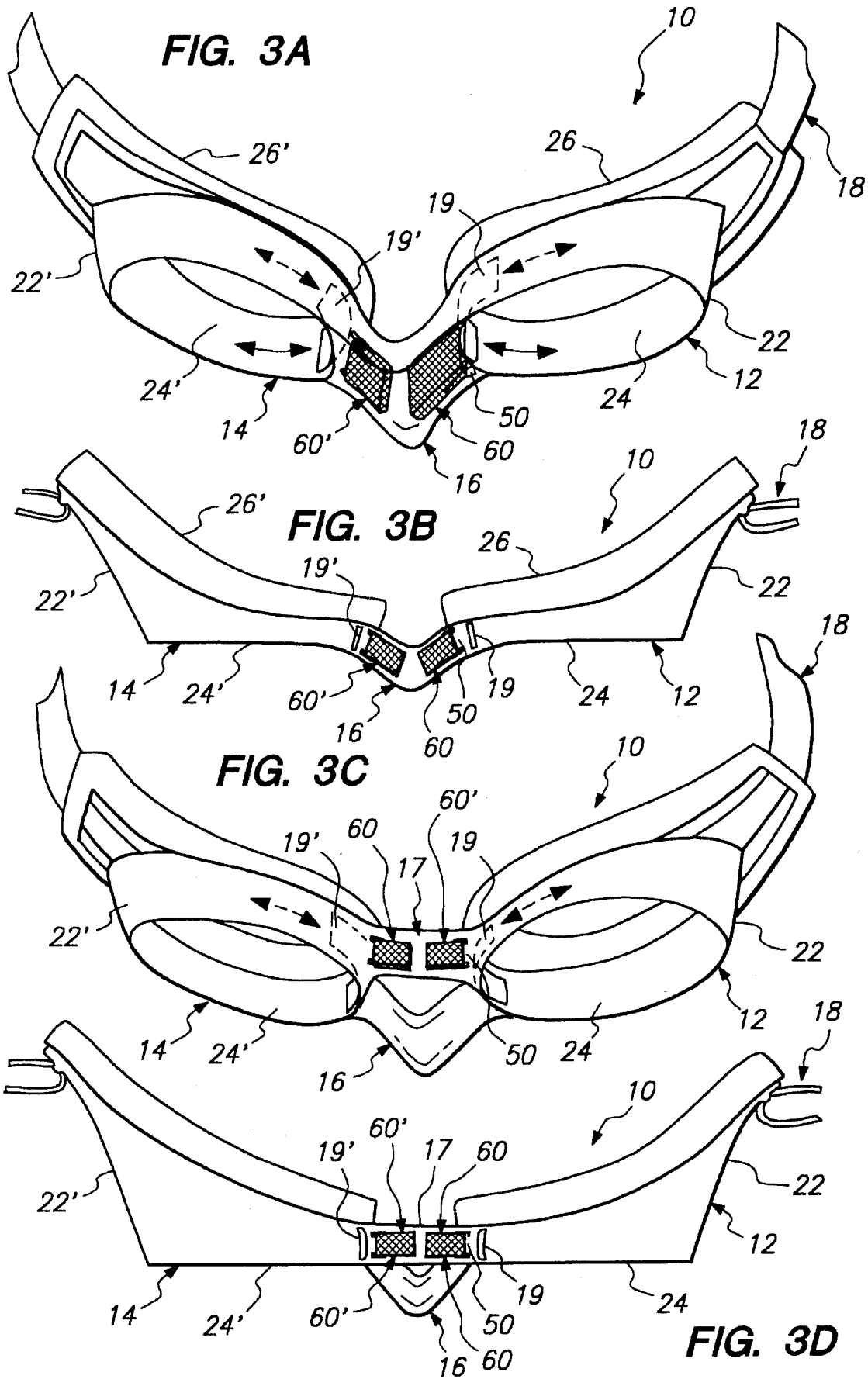

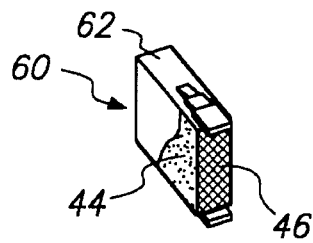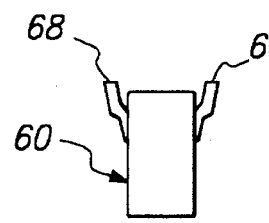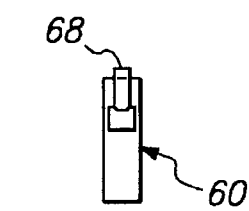
FIG. 3E     FIG. 3F     FIG. 3G
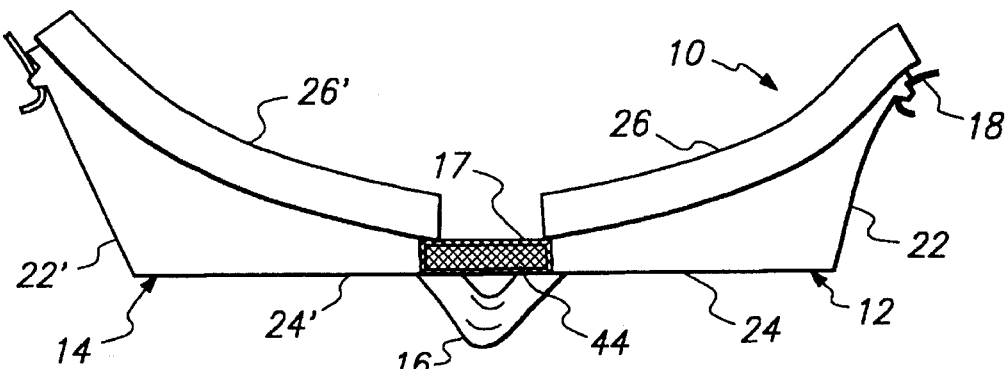
FIG. 4A
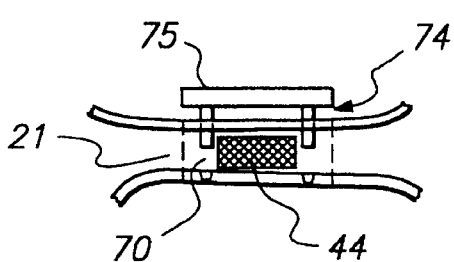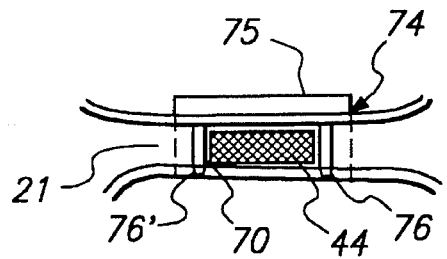
FIG. 4B     FIG. 4C
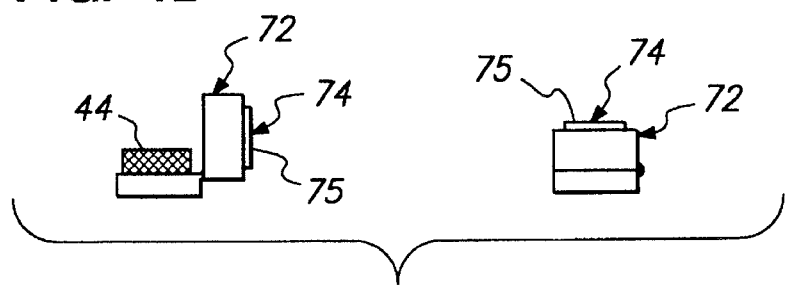
FIG. 4D
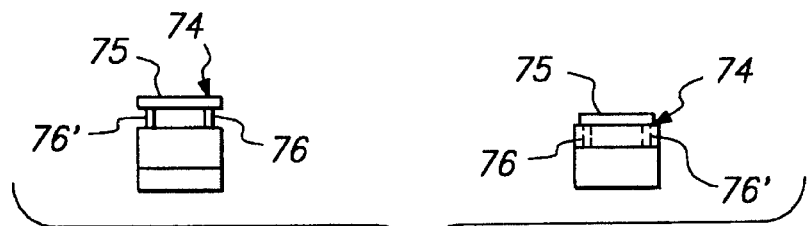
FIG. 4E

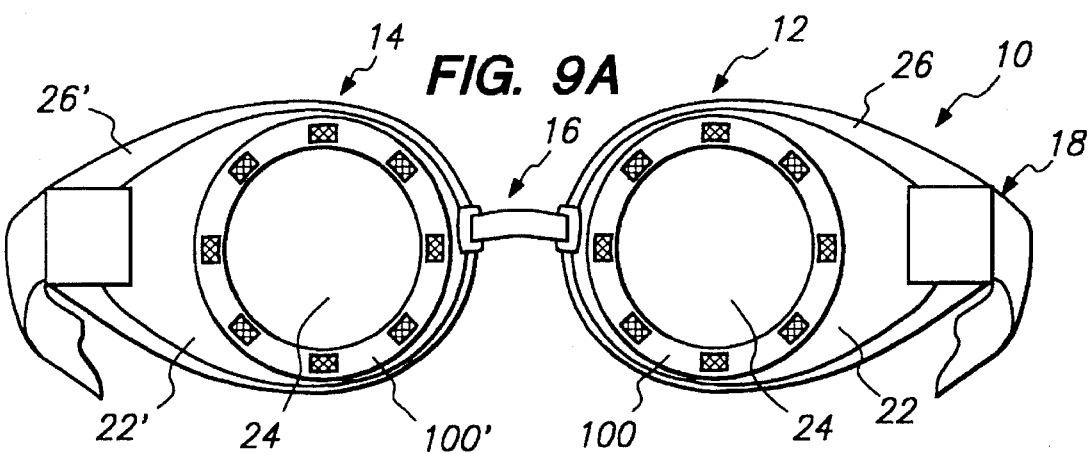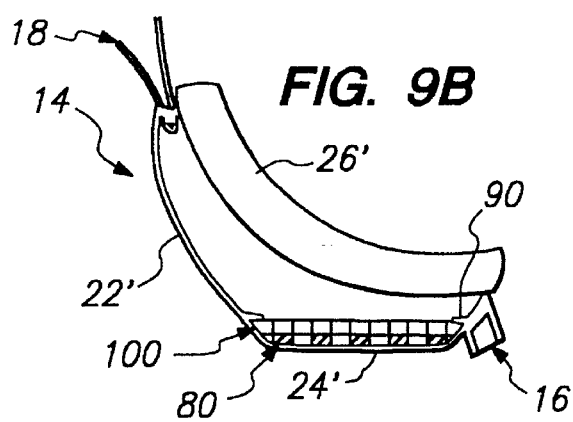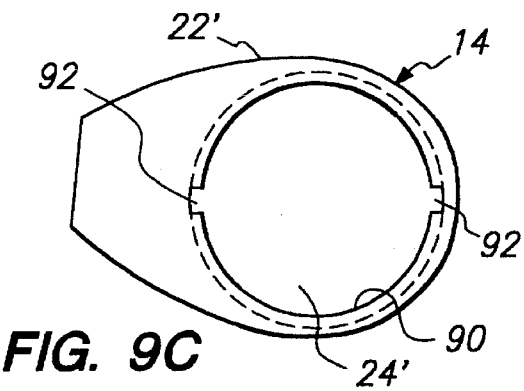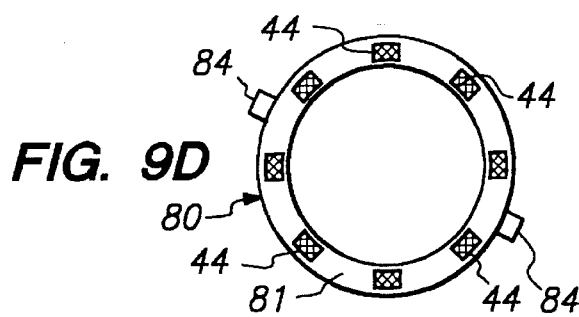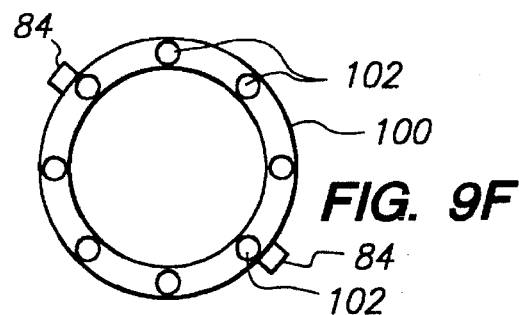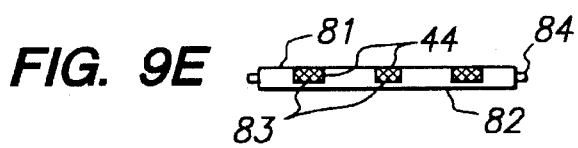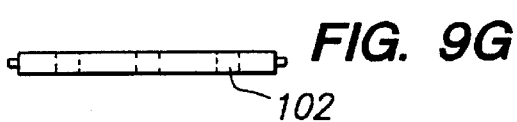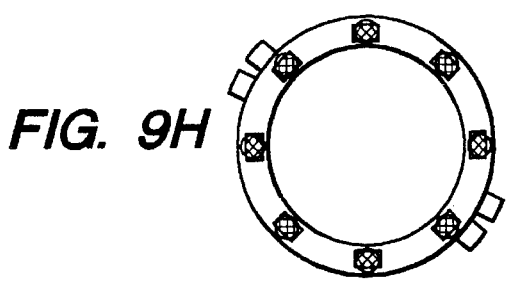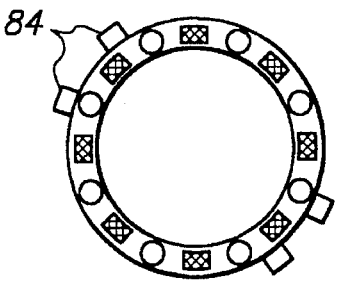

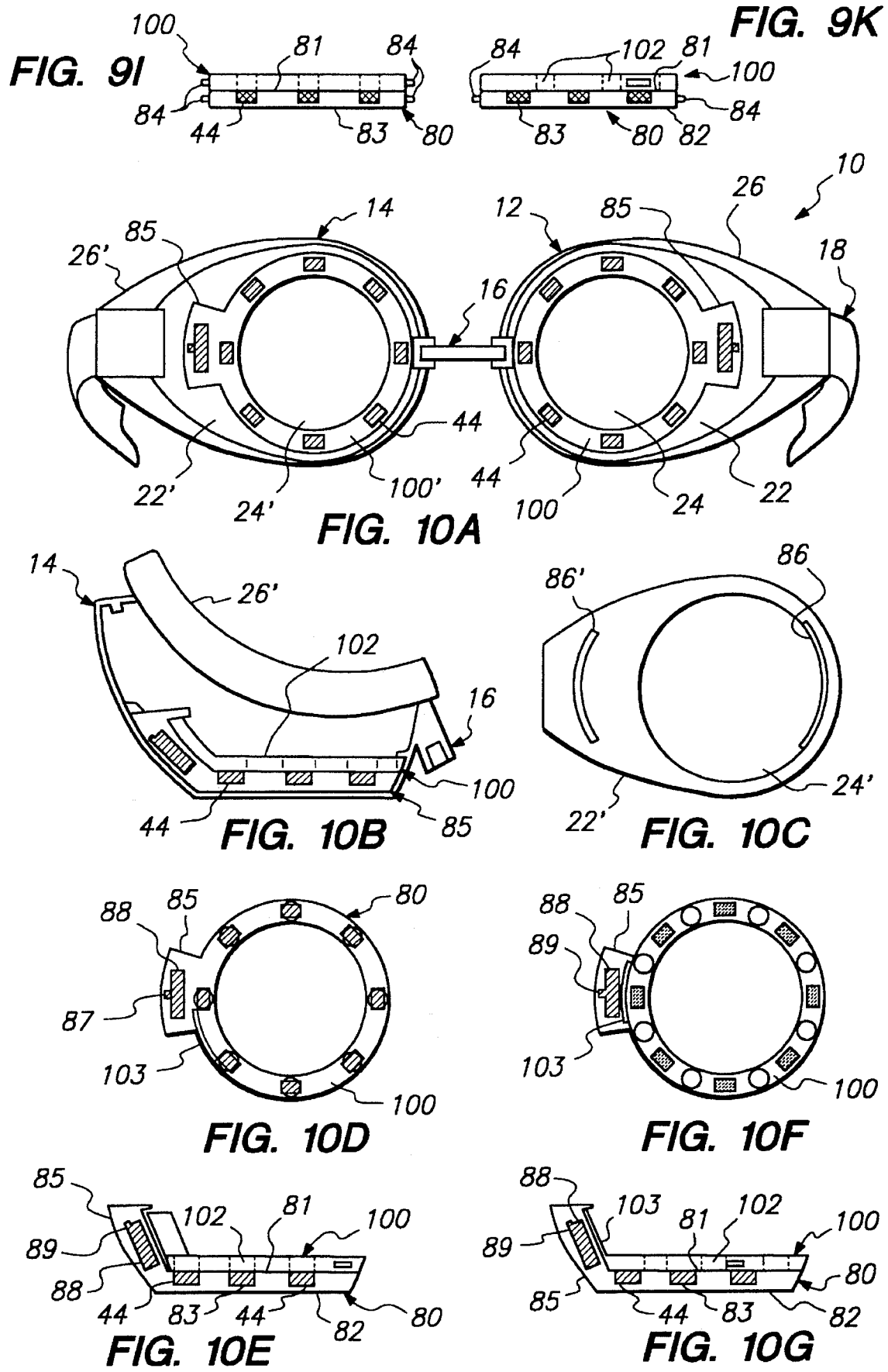

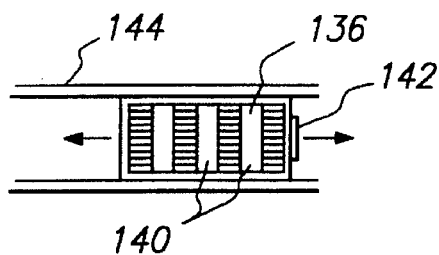
FIG. 14D
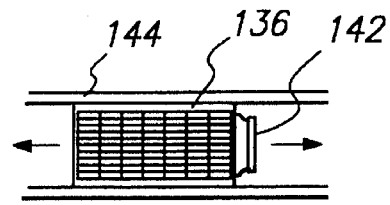
FIG. 14F
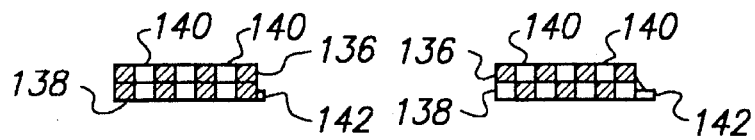
FIG. 14E    FIG. 14G
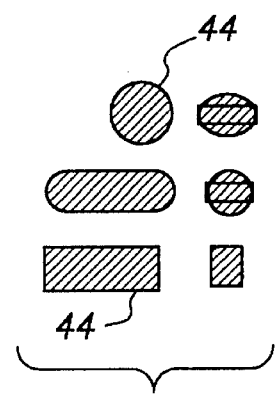
FIG. 14L
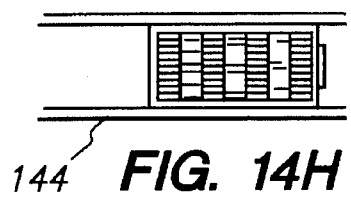
FIG. 14H
FIG. 14J
FIG. 14I
FIG. 14K
FIG. 14M
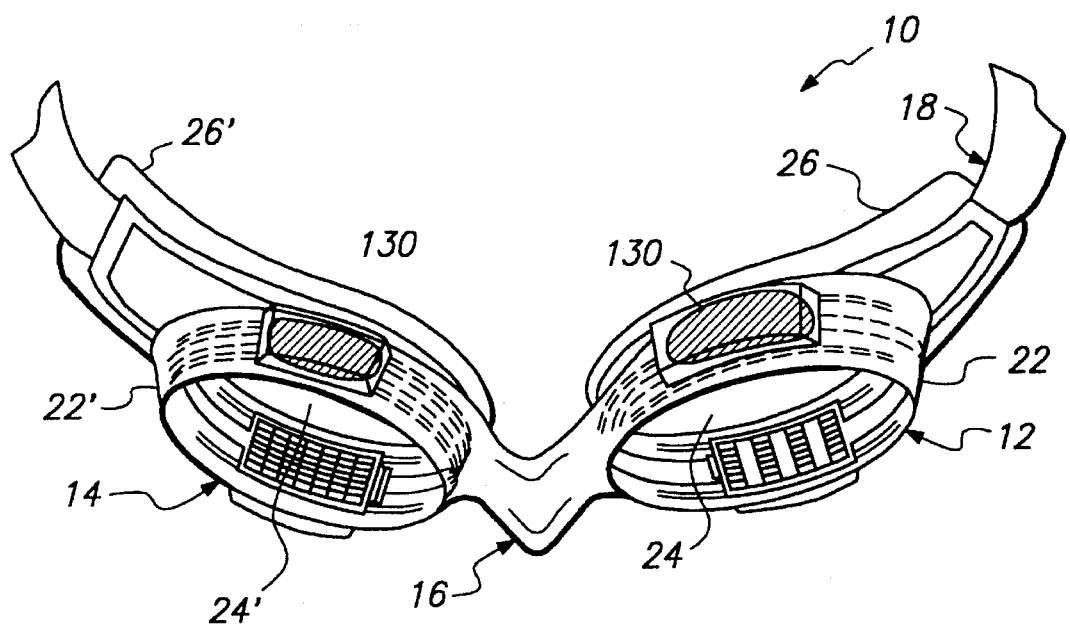
FIG. 15A

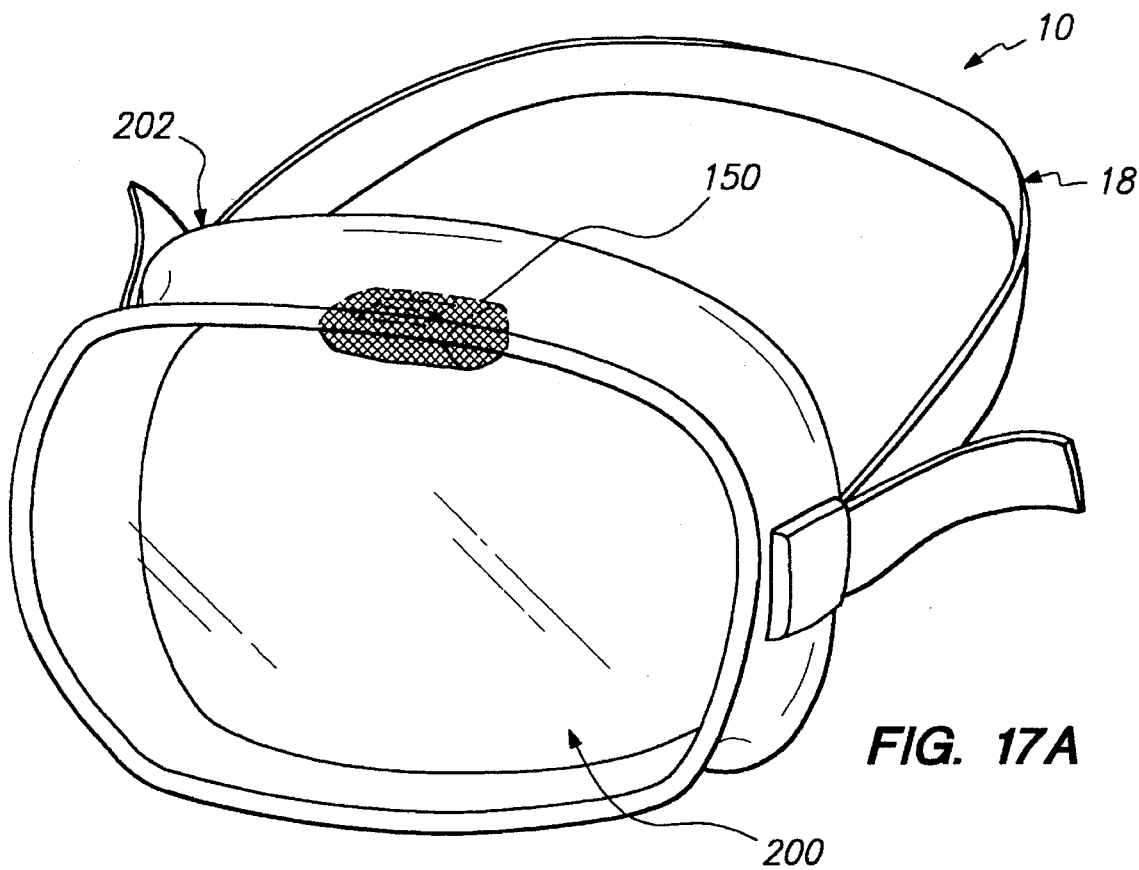
FIG. 17A
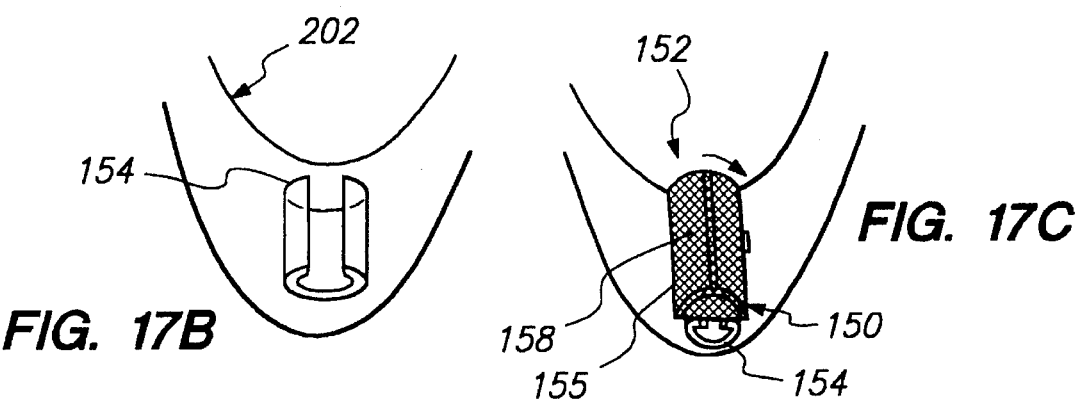
FIG. 17B　　FIG. 17C
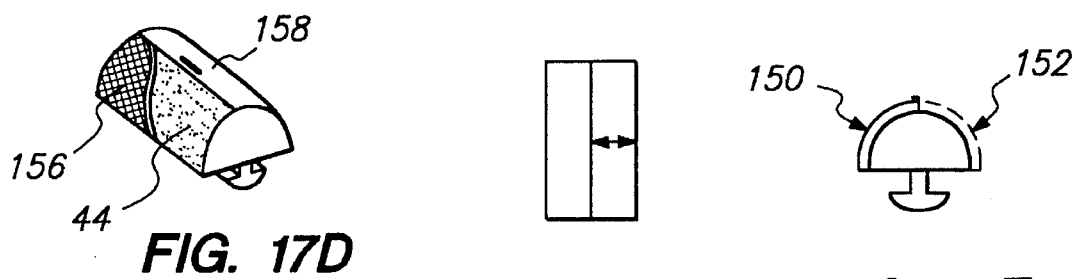
FIG. 17D　　FIG. 17E　　FIG. 17F

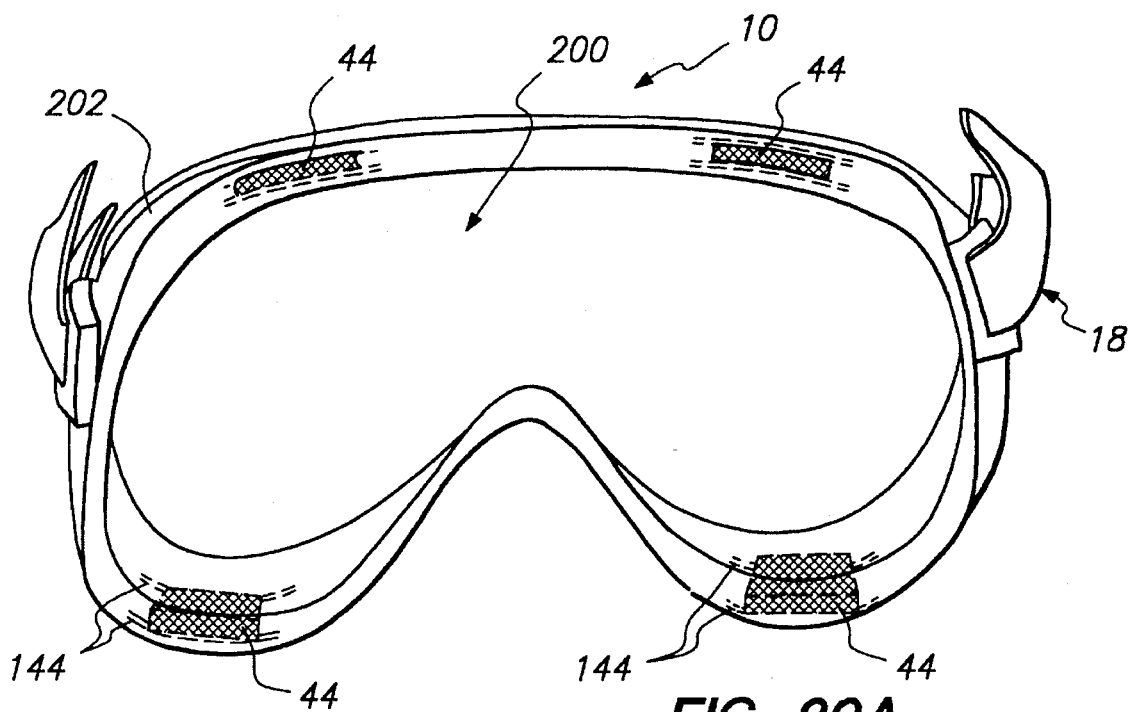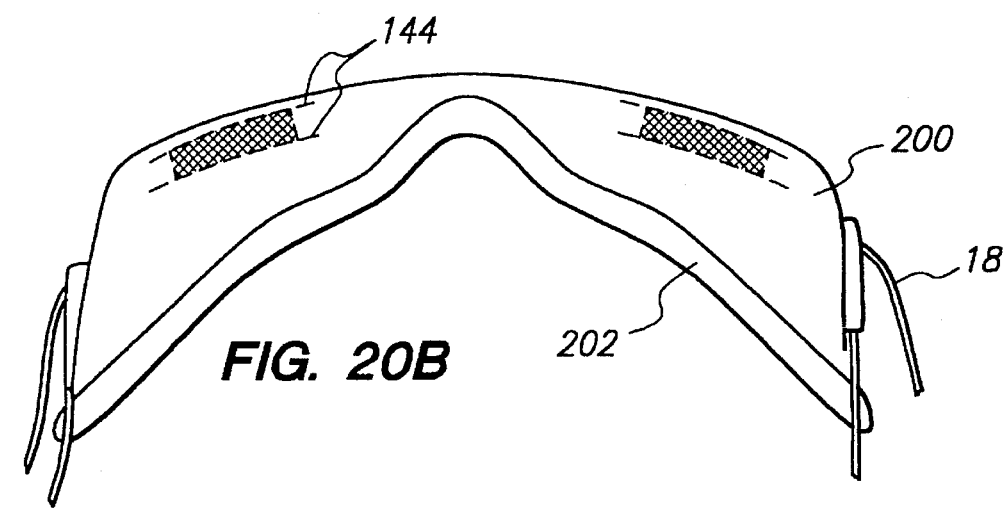

GOGGLE AND DESICCANT ASSEMBLY

FIELD OF THE INVENTION

The invention relates generally to athletic goggles and masks used for swimming, skiing and like sports, and more particularly to goggles and masks incorporating desiccant assemblies.

BACKGROUND OF THE INVENTION

Manufacture and sale of athletic goggles and masks is a multi-million dollar industry world-wide. Ski masks, swim goggles and the like are designed to protect a user's eyes from injury and uncomfortable contact with water or air. This is achieved by providing the goggles or mask with an air tight seal that conforms to the user's face to create pockets of air around the user's eyes, and thereby separate the eyes from the harsh external medium.

Notwithstanding the large number of different types of goggles and masks offered to the public, all suffer from a recurrent and bothersome problem: the deposition of minute water droplets, commonly known as "fogging," on the interior surface of the eye pieces. Fogging generally occurs because of a temperature differential between the mask or goggles, which tend to attain the temperature of the external medium, and the pockets of air trapped within the goggles, which tend to remain at a temperature closer to the skin temperature of the user. Water vapor in the trapped air pockets cools upon contact with the cooler surfaces of the goggles and condenses as water droplets on these surfaces. The problem is further exacerbated by the fact that moisture from the skin, and more particularly the ocular surface, of the user evaporates during athletic activity, saturating the trapped air with more water vapor even as pre-existing water vapor is lost as droplets through condensation.

Fogging is problematic because it results in a significant loss of visibility, requiring the user to cease athletic activity frequently in order to defog the goggles or mask manually. This is particularly disadvantageous during an athletic competition where the loss of even a few seconds can result in the loss of a race.

Although many solutions have been proposed to the fogging problem, none is without significant drawbacks. For example, it is known that coating the lens with a thin film of a hydrophobic material, such as oil or soap residue, can alleviate problems with fogging. However, such materials frequently impair visual acuity through the lens and require frequent reapplication. U.S. Pat. Nos. 4,972,521 to Lison and 4,414,693 to Brody each describe eyewear comprising lenses coated with more permanent anti-fogging material. Although overcoming the reapplication problem, fogging is not completely eliminated. Furthermore such manufactures are too difficult and expensive to produce for applications that do not require a high degree of optical precision, such as prescription eye glasses and the like.

Others have approached the fogging problem by designing intricate assemblies in an attempt to isolate fog-prone lens surfaces from the conditions that promote fogging, such as extreme temperature differentials between the interior and exterior of masks and goggles. U.S. Pat. Nos. 3,591,864 to Allsop and 5,018,223 to Dawson et al., which teach the use of spaced apart lenses, are illustrative of this approach. Such constructions are extremely costly to produce and too delicate to employ in active wear such as athletic goggles and masks.

In view of long the long felt need within the industry to solve the fogging problem and the short-comings inherent in the prior art, there is clearly a need for a safe, effective, and affordable means of eliminating fogging in athletic goggles and masks. Such a solution should not only be effective, but it must be efficient to manufacture, cost-effective to produce, and carefree to use. It must also be easy to adapt for use in retrofitting the many millions of existing goggles and masks currently in use.

SUMMARY OF THE INVENTION

Therefore, it is an object of the invention to provide means for eliminating fogging of interior lens surfaces of goggles and athletic masks during use.

It is another object of the invention to provide a means for eliminating fogging that does not require the application of hydrophobic films, such as oil or soap residue.

It is a further object of the invention to provide a means for eliminating fogging that is structurally effective and efficient to manufacture.

Yet another object of the invention is to provide a means for eliminating fogging that is convenient to use and that does not require substantial maintenance on the part of the goggle or mask user.

A further object of the invention is to provide a means for eliminating fogging that can be effectively added to existing goggles and masks that lack such a means.

The invention meets these objects by providing a goggle or mask assembly that includes an effective desiccant means. The desiccant means of the invention comprises a desiccant, such as $SiO_2$ or the like, captured within a desiccant housing or a desiccant chamber. The desiccant may be preferentially provided with an indicator substance that noticeably changes color as the desiccant becomes saturated with water. The desiccant housing may further be provided with a semi-permeable membrane that permits the passage of water vapor, but prevents passage of liquid water, through the desiccant housing. The desiccant means is positioned at a desired point along an interior surface of the goggles or mask, or within a portion of the goggles or mask, such that the semi-permeable membrane of the desiccant housing is in gaseous communication with the air reservoirs captured by the goggles or mask when worn by a user.

In operation, the assembly of the invention is positioned over the face of the user to provide an air tight seal, thereby capturing a reservoir of air around each of the user's eyes. During use, water vapor present in the captured air reservoirs passes into the desiccant means where it is absorbed by the desiccant. Until such time as the desiccant reaches saturation, the rate of absorbance exceeds the evaporation rate from the skin and eyes into the captured air reservoirs. As a result, relative humidity within the captured air reservoirs remains low, preventing the formation of fog on the interior surfaces of the assembly.

In another embodiment, the desiccant means is provided with closure means, such as a sliding or rotating door, that isolates the desiccant from the external environment. This is advantageous in that continuing operation of the desiccant can be halted when the assembly is not in use, thereby greatly prolonging the lifespan of the desiccant.

In yet another embodiment of the invention, the goggles or masks are provided with chambers into which desiccant or disposable desiccant packets can be placed. The chambers are provided with lids that can be popped open for desiccant insertion. The chambers are further provided with openings to the interior captured air pockets, which may be provided with water vapor permeable membranes if desired. When the desiccant is added in packet form, the packets are provided with water vapor permeable membranes, thereby obviating the need to provide similar membranes in the desiccant chambers.

According to a further embodiment of the invention, the desiccant means can be configured as a retrofit for pre-existing goggles and masks. The retrofit comprises a desiccant chamber and an attachment means. The attachment means is affixable to a suitable interior surface of a mask or pair of goggles, and is configured to receive and/or release the desiccant chamber. The desiccant chainbet may contain a non-encapsulated form of a suitable desiccant or the desiccant may be captured within a desiccant housing having a water vapor-permeable membrane, with the desiccant housing retained within the desiccant chamber.

The invention is significantly advantageous over the prior art in that it provides for the first time a mechanically efficient, functionally effective and affordable means for preventing the fogging of interior ocular surfaces, a common and annoying problem encountered by the users of air-tight protective goggles and masks. The construction of the invention translates not only into significant production cost savings, thereby lowering cost to the consumer, but also makes possible the rapid retrofit of pre-existing goggles and masks currently in use. The invention is further advantageous in that the user need provide no maintenance other than periodic replacement of the desiccant.

These and other advantages of the invention will become apparent upon consideration of the figures and the detailed description of the invention set forth below.

BRIEF DESCRIPTION OF THE DRAWINGS

FIG. 1A is a view in perspective of a first embodiment of the assembly of the invention. FIG. 1B is a top view of an eye-cup of the assembly shown in FIG. 1A. FIG. 1C is a side view of an eye-cup of the assembly shown in FIG. 1A. FIG. 1D is a front view of the desiccant capsule of the assembly shown in FIG. 1A. FIG. 1E is a lateral view of the desiccant capsule of the assembly shown in FIG. 1A. FIG. 1F is a top view of the desiccant capsule of the assembly shown in FIG. 1A. FIG. 1G is a partial cross-section of the eye-cup shown in FIG. 1B and 1C showing the desiccant chamber empty. FIG. 1H is the same view as shown in FIG. 1G showing the desiccant capsule positioned in non-operative position within the desiccant chamber. FIG. 1I is the same view as shown in FIG. 1H showing the desiccant capsule operative position within the desiccant chamber.

FIG. 2A is a view in perspective of a second embodiment of the assembly of the invention. FIGS. 2B and 2C are top and side views respectively of an eye-cup of the assembly shown in FIG. 2A. FIG. 2D is a partial cross-section of the eye-cup of FIGS. 2B and 2C showing the insertion chamber for the desiccant chamber. FIG. 2E is a view in perspective of the desiccant capsule with the housing of the desiccant capsule partially cut away to expose the desiccant.

FIGS. 3A and 3B are views in perspective and from above of a third embodiment of the assembly of the invention. FIGS. 3C and 3D are views in perspective and from above of a fourth embodiment of the assembly of the invention. FIGS. 3E, 3F and 3G are a partial cut-away view in perspective, a front view and a side view respectively of second embodiment of the desiccant capsule of the invention.

FIG. 4A is a top view of a fifth embodiment of the assembly of the invention. FIGS. 4B and 4C are cross sectional front views of the desiccant chamber of the assembly of FIG. 4A in operative and non-operative configuration respectively. FIG. 4D is a side view of the desiccant chamber of the assembly in FIG. 4A in both open and closed configuration for receipt of a desiccant capsule. FIG. 4E is a side view of the desiccant chamber of the assembly in FIG. 4A in both operative and nonoperative configurations.

FIG. 9A is a front view of a eighth embodiment of the invention. FIGS. 9B and 9C are side and top views respectively of the eye-cup shown in FIG. 9A. FIGS. 9D and 9E are top and side views of the desiccant capsule of embodiment. FIGS. 9F and 9G are top and side views of the desiccant capsule overlay of the embodiment. FIG. 9H and I are top and side views respectively of the desiccant capsule and desiccant capsule overlay in assembled operative configuration. FIG. 9J and 9K are top and side views respectively of the desiccant capsule and desiccant capsule overlay in assembled non-operative configuration.

FIG. 10A is a frontal view of an ninth embodiment of the assembly of the-invention. FIGS. 10B and 10C are side and top views respectively of the eye-cup of embodiment. FIGS. 10D and 10E are top and side views respectively of the desiccant capsule of the embodiment. FIGS. 10F and 10G are top and side views respectively of the desiccant capsule overlay of the embodiment.

FIGS. 14D and 14E are top and side views respectively of the gate of the desiccant chamber in an open, operative configuration. FIGS. 14F and 14G are top and side views respectively of the gate of the desiccant chamber in a closed, non-operative configuration. FIGS. 14H and 14I are the same view as shown in FIGS. 14D and 14E, except that the gate is further provided with a water vapor permeable screen. FIGS. 14J and 14K are top and side views of the water vapor permeable screen of FIGS. 14H and 14I. FIG. 14L shows some tablet configurations of a naked desiccant. FIG. 14M shows the desiccant encapsulated within a bag incorporating a water vapor permeable membrane.

FIG. 15A is a view in perspective of a fourteenth embodiment of the invention.

FIG. 17A is a view in perspective of a diving mask incorporating the desiccant retrofit of the invention according to a sixteenth embodiment of the invention. FIG. 17B is a close up of the attachment means of the desiccant retrofit of the invention. FIG. 17C is a close up of the desiccant chamber coupled with the attachment means shown in FIG. 17B. FIG. 17D is a view in perspective of the desiccant capsule of the invention, showing door means. FIGS. 17E and 17F are top and side views respectively of the desiccant capsule of FIG. 17D.

FIGS. 19B and 19C are top views of the gate of the desiccant assembly in operative and non-operative views respectively. FIG. 19D is the same view as shown in FIG. 19B further including a water permeable screen. FIG. 19E is a top view of the water permeable screen of FIG. 19D.

FIG. 20A is a view in perspective of a mask according to a eighteenth embodiment of the invention. FIG. 20B is a top view of the mask shown in FIG. 20B.

DETAILED DESCRIPTION OF THE INVENTION

Figure 5A:
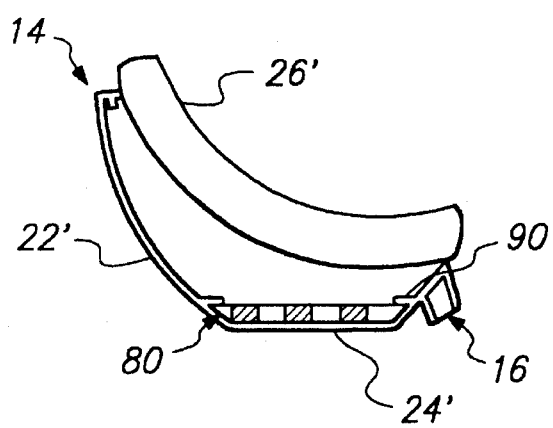
FIGS. 5A and 5B are a side and top view in partial cross section and a front view respectively of an eye-cup of a fifth embodiment of the assembly of the invention.
Figure 5B:
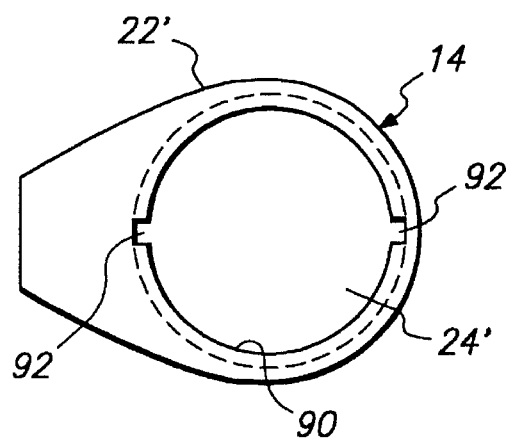

Turning now to the figures, the assembly of the invention will now be described. Although the assembly will generally be described and illustrated with respect to swim goggles, it will be appreciated that the invention pertains to any protective athletic mask or goggles designed to form an air tight sealed around one or both eyes of the user.

A first and second goggle assembly embodiments are shown in FIGS. 1 and 2. The goggle assembly 10 comprises a left eye-cup 12, a right eye-cup 14, a nose piece 16, and a strap 18. Each of eye-cups 12 and 14 is further characterized in comprising lenses 20 and 20' and air tight seals 26 and 26' respectively. Each of lenses 20 and 20' is further characterized in having limbs 22 and 22' and panes 24 and 24' respectively.

In the first embodiment, shown, in FIG. 1, limbs 22 and 22' are provided with a desiccant chamber 30 and a desiccant capsule 40 on their outer peripheries. Desiccant capsule 40 is generally cylindrical in shape, and is configured to slide within the desiccant chamber 30. In the present embodiment, desiccant capsule 40 comprises a housing 42 that captures a desired desiccant 44. The housing 42 is provided with a water vapor permeable membrane 46 that allows the passage of water vapor into the housing, but prevents the passage of liquid water, thereby preventing the desiccant from becoming prematurely quenched. One such suitable water vapor permeable membrane, termed GDT, is polyester/polypropylene and is generally commercially available. Another suitable membrane is spun-bonded olefin, as set forth and described in U.S. Pat. No. 3,990,872 to Cullen, the contents of which are expressly incorporated herein by reference. Such spun-bonded olefin membranes can be obtained commercially from the DuPont Company under the brand name Tyvek®.

Figure 16A:
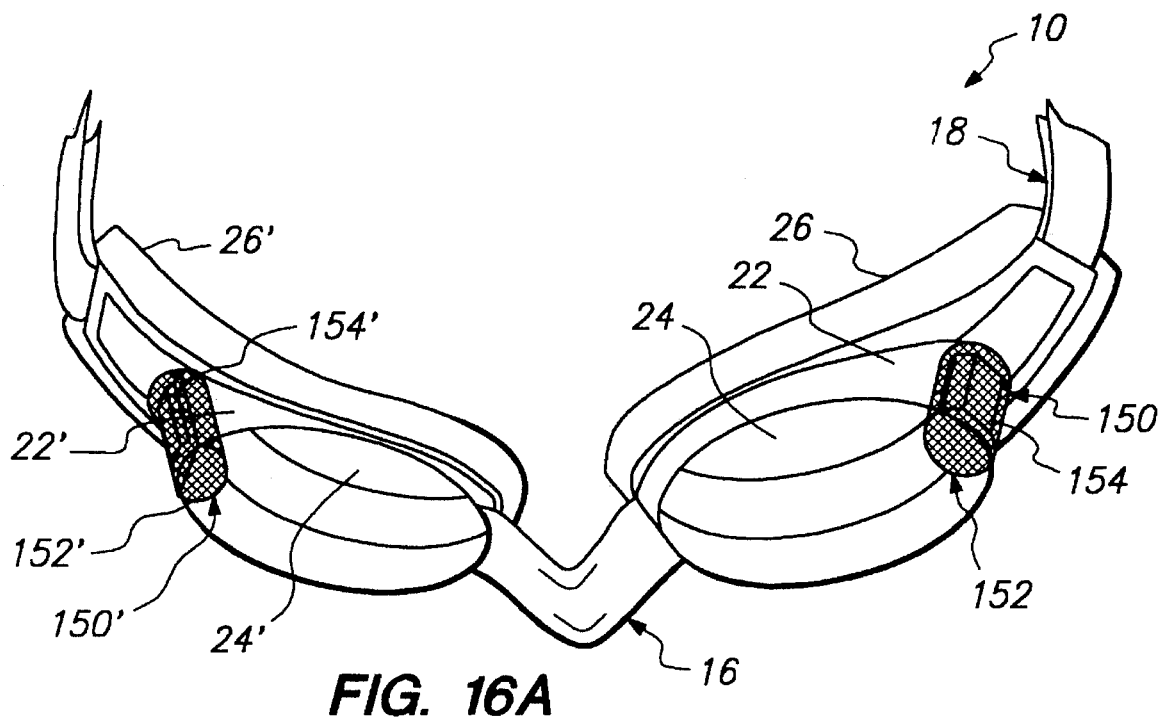
FIG. 16A is a view in perspective of goggles retrofitted with desiccant capsules according to a fifteenth embodiment of the invention.
Figure 16B:
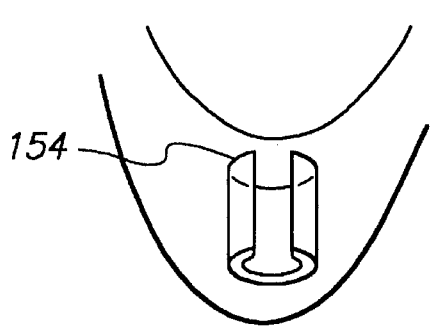
FIG. 16B is a close-up of the attachment means of the desiccant retrofit of the invention.
Figure 16C:
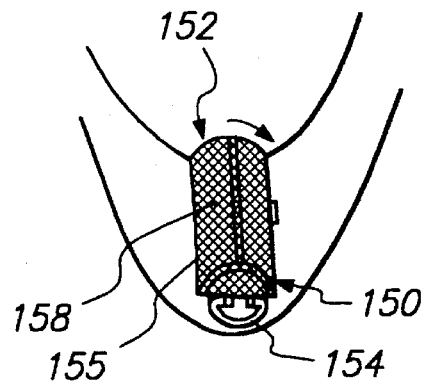
FIG. 16C is a close-up of the desiccant chamber coupled with the attachment means shown in FIG. 16B.
Figure 16D:
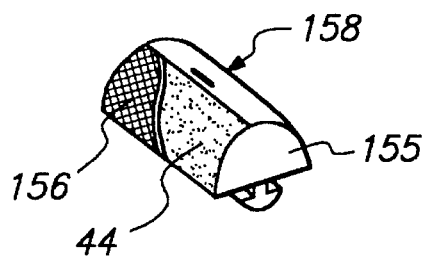
FIG. 16D is a view in perspective of the desiccant capsule of the invention, showing door means.
Figure 16E:
FIGS. 16E and 16F are top and side views respectively of the desiccant capsule of FIG. 16D.
Figure 16F:
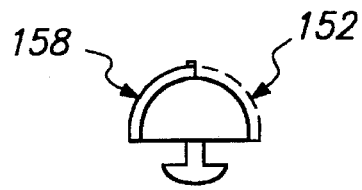
Figure 18:
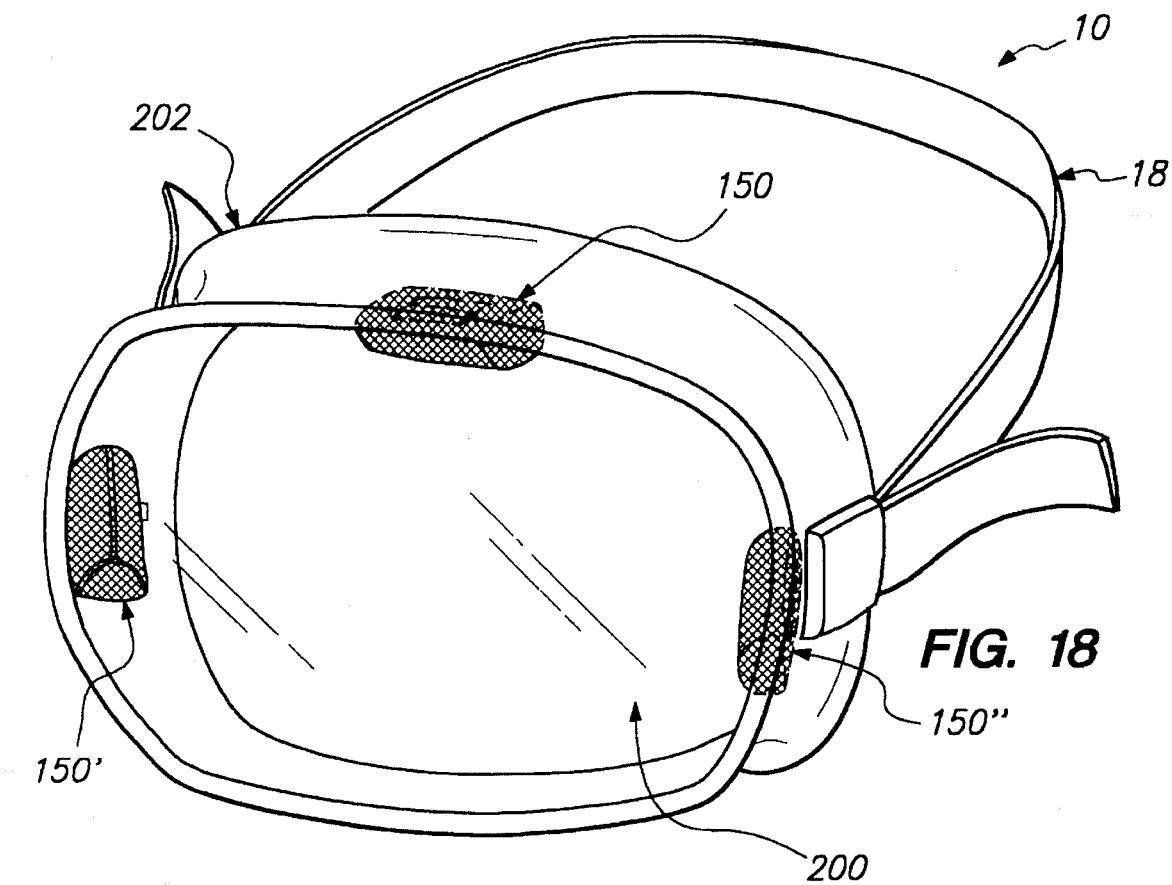
FIG. 18 is a further view of the mask shown in FIG. 17A equipped with additional retrofit desiccant assemblies.

Desiccant housing 42 is further provided with prongs 48, as shown in FIGS. 16D through 16F. These prongs permit desiccant capsule 40 to be clipped into place within desiccant chamber 30. Desiccant chamber 30 is configured for snug receipt of desiccant capsule 40, and is provided with prong tracks 32 for reversible receipt of prongs 48 of desiccant capsule 40. Desiccant chamber 30 is further provided with a port 34. Port 34 is configured to align with water vapor permeable membrane 46 of desiccant capsule 40 as shown in FIG. 1I. In such configuration, continuous contact is maintained between the desiccant 44 in the desiccant capsule 40 and the air trapped between the goggle assembly 10 and the face when the goggle assembly is in use. When not in use, desiccant capsule 40 can be snapped into an alternate position whereby the wall of desiccant chamber 30 covers water vapor permeable membrane 46, as shown in FIG. 1F. In such a position, contact between the atmosphere and desiccant 44 is blocked, thereby lengthening the effective life of the desiccant.

It will be noted that the desiccant chamber 30 of the embodiment shown in FIG. 1 is formed exterior to limb 22 of left and right eye-cups 12 and 14. Alternatively, desiccant chamber 30 can be formed interior of limb 22, as shown in FIG. 2, but is similar in all other respects to the embodiment just described.

In another embodiment of the invention, as shown in FIGS. 3 and 4, desiccant 44 is placed within nose piece 16 or within a bridge 17 above nose piece 16. In each instance, nose piece 16 and bridge 17 are provided with a desiccant chamber 50 proximate to each of eye-cups 12 and 14. As in the previous embodiment, desiccant 44 is encapsulated within a desiccant housing 62 to provide a desiccant capsule 60, except in the present embodiment desiccant capsule 60 is roughly pylon-shaped. Desiccant housing 62 is further provided with prongs 68 for reversible attachment of the desiccant capsule 60 along prong tracks (Not shown) within the desiccant chambers 50. Desiccant housing 62 is also provided with a water vapor permeable membrane 46 at the end of the housing that remains exposed after insertion of the housing into desiccant chamber 50, as shown in FIGS. 3A, 3C, and 3E.

Because the configurations of the desiccant chamber 50 and desiccant capsule 60 do not permit water permeable membrane 46 to be blocked when desiccant capsule 60 is inserted desiccant chamber 50, nose piece 16 and bridge 17 are provided with one or more doors 19 and 19'. Doors 19 and 19' are slidably mounted on limb 22 and 22' of each of eye-cups 12 and 14 proximate to the opening of each desiccant chamber 50 and 60. When goggles assembly 10 is in use, doors 19 and 19' are retracted from the openings of desiccant chambers 50, thereby exposing water vapor permeable membranes 46 of desiccant capsules 60 to air trapped within goggles assembly 10. In such configuration, water vapor from the trapped air enters desiccant capsules 50 and is absorbed by desiccant 44. When the goggles are not in use, desiccant 44 is spared unwanted exposure to water vapor by moving doors 19 and 19' over the openings of desiccant chambers 50, thereby blocking water vapor permeable membranes 46 and cutting off atmospheric contact with desiccant 44.

Bridge 17 can also be provided with a through passage 21 for flip-top loading of a solid mass of desiccant or desiccant capsule, as shown in FIG. 4. In this embodiment, bridge 17 is provided with a desiccant chamber 70 having a snapping flip-top 72. Desiccant 44 is loading into desiccant chamber 70, and flip top 72 is snapped shut. Flip top 72 is further provided with a gate 74 having a pull 75 and closure panels 76 and 76', as shown in FIGS. 4B and 4C. When goggle assembly 10 is not in use, gate 74 is pushed downward, as shown in FIG. 4C, so that panels 76 securely engage the walls of bridge 17 and form an air-tight seal around desiccant 44, thereby cutting off atmospheric contact and unnecessary exposure to water vapor. When worn, the user pulls gate 74 up into the open position, as shown in FIG. 4B, thereby establishing air contact between desiccant 44 and the reservoirs of air captured between the eye-cups of the goggles and the face of the user.

In another series of embodiments according to the invention, the desiccant capsule can be configured as a ring to be snugly received within limb 22 of the eye-cup. These embodiments are illustrated in FIGS. 5–13. Desiccant 44 may be sequestered within the capsule matrix, and continuously exposed to the air, such as is shown in FIGS. 5–7, or may be part of a desiccant assembly, comprising not only the desiccant capsule, but a ring shaped gate that is rotatable above and is capable of closing off the desiccant capsule from unwanted atmospheric contact when the goggles assembly is not in use. These embodiments are illustrated in FIGS. 9–12.

Figure 5C:
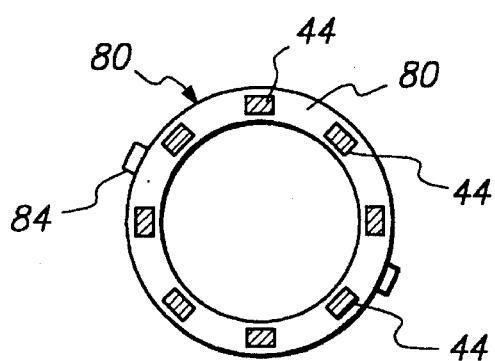
FIGS. 5C and 5D are top and side views respectively of the desiccant capsule of FIG. 5A.
Figure 5D:
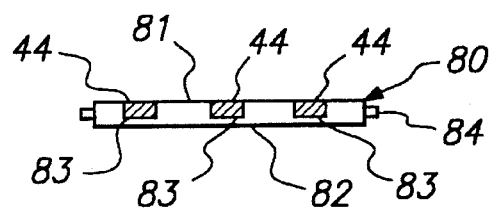
Figure 6A:
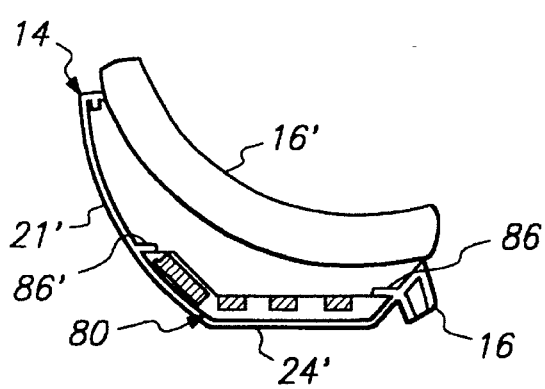
FIG. 6A and 6B are front and top views of an eye-piece of a sixth embodiment of the invention.
Figure 6B:
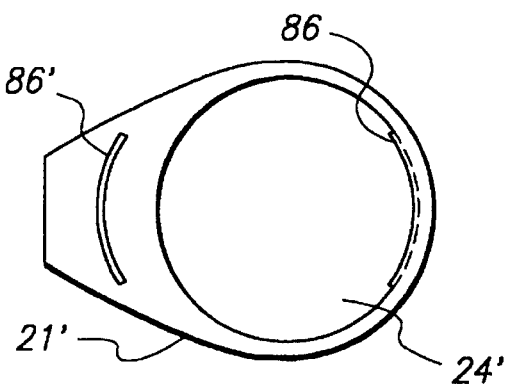
Figure 6C:
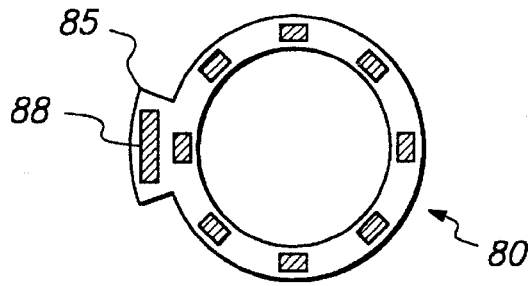
FIGS. 6C, 6D and 6E are a top, side and front view of the desiccant capsule of the embodiment.
Figure 6D:
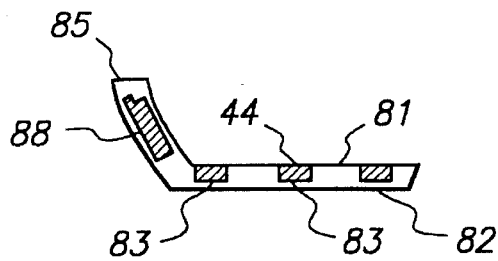
Figure 6E:
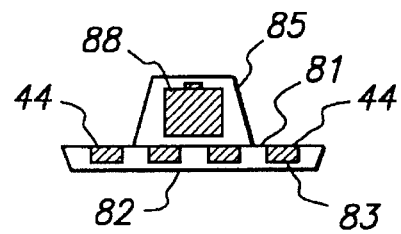
Figure 6F:
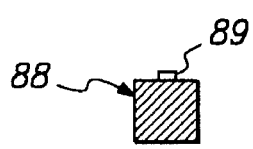
FIGS. 6F, 6G, and 6H are front, side and rear views respectively of the desiccant capsule of the embodiment.
Figure 6G:
Figure 6H:
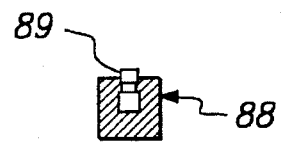
Figure 7A:
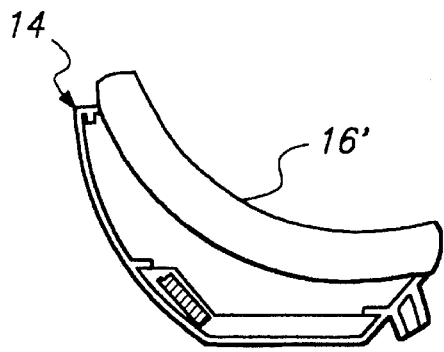
FIG. 7A and 7B are side and top views respectively of an eye-piece a seventh embodiment of the assembly of the invention.
Figure 7B:
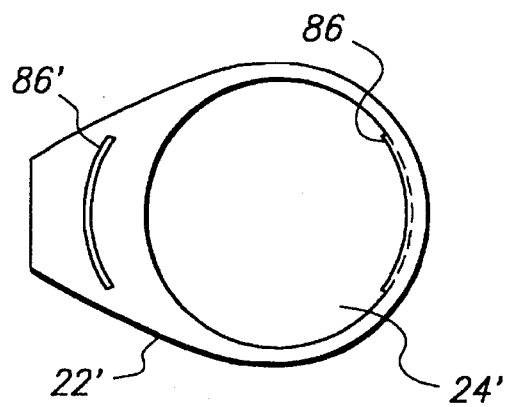
Figure 7C:
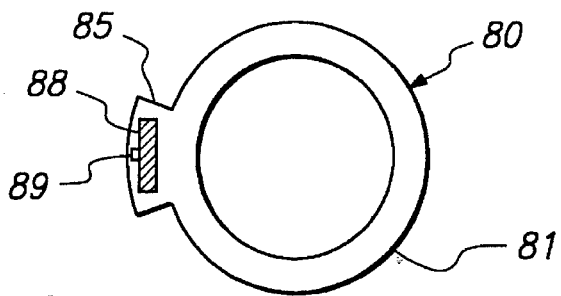
FIGS. 7C, 7D and 7E are top, side and front views respectively of the desiccant capsule of the embodiment.
Figure 7D:
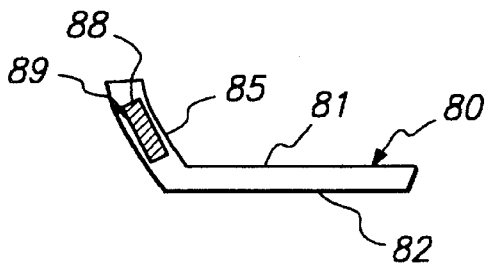
Figure 7E:
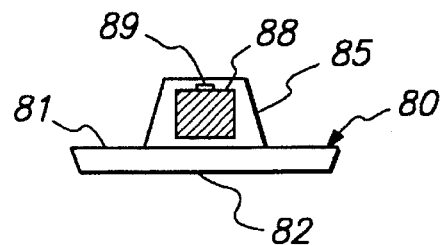
Figure 8:
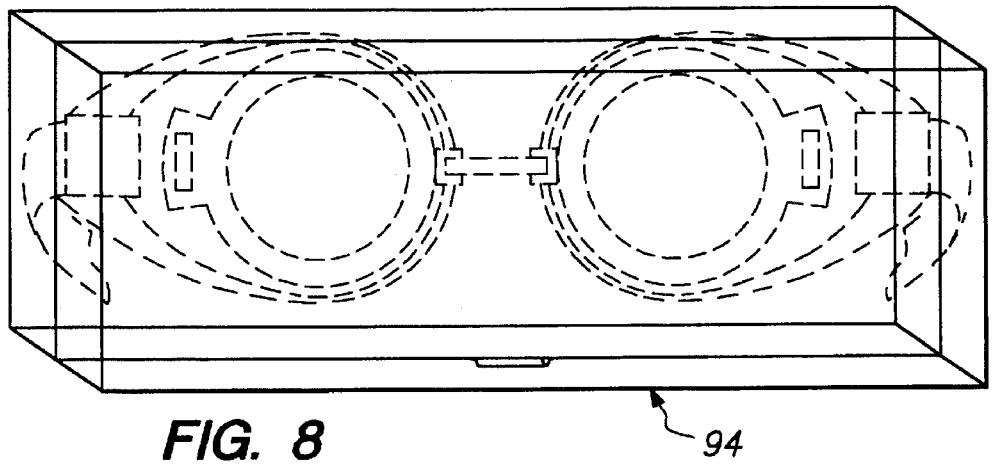
FIG. 8 is a view in perspective of an air-tight carrying case for the goggles assembly of the invention.
Figure 10H:
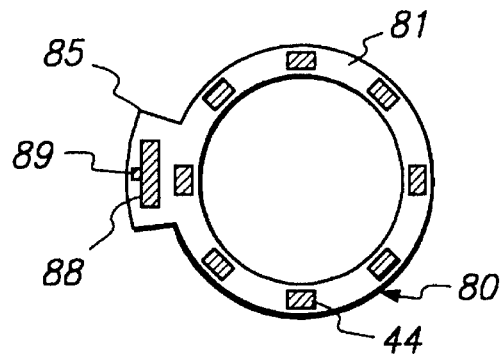
FIGS. 10H and 10I are top and side views respectively of the desiccant capsule.
Figure 10J:
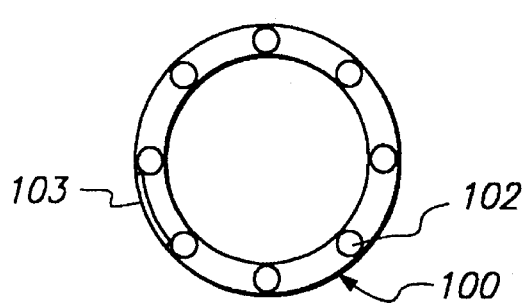
FIGS. 10J and 10K are top and side views respectively of the desiccant capsule overlay.
Figure 10I:
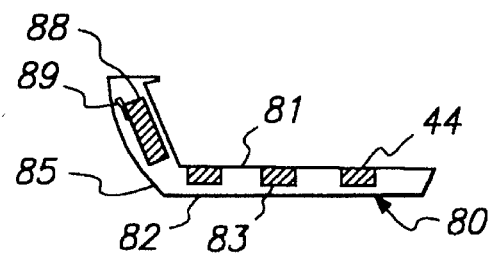
Figure 10K:
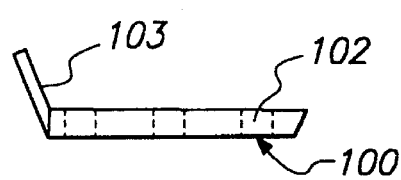
Figure 11A:
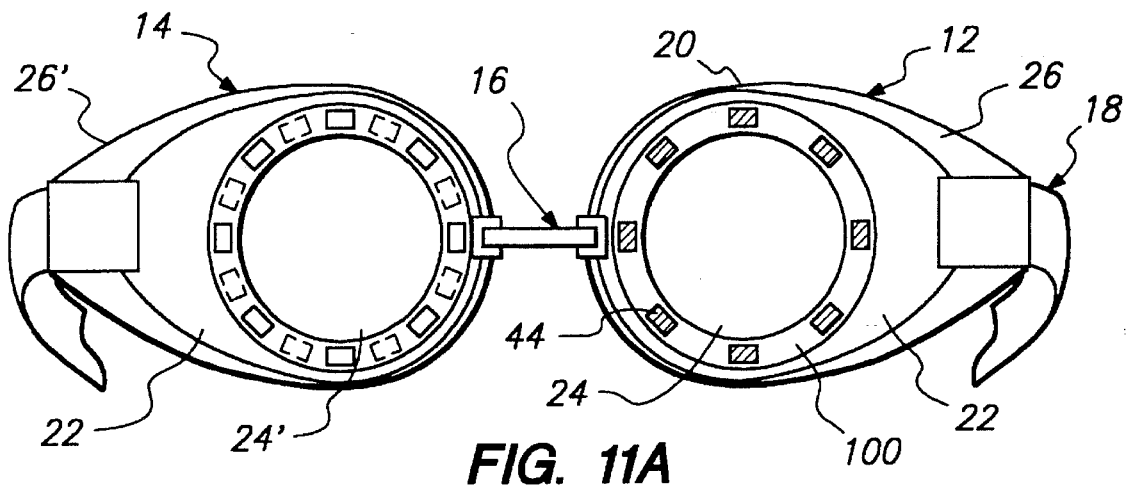
FIG. 11A is a frontal view of a tenth embodiment of the assembly of the invention.
Figure 11B:
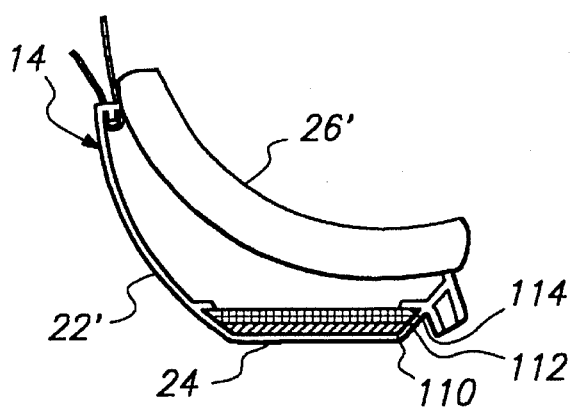
FIGS. 11B and 11C are side and top views respectively of the eye-cup of the embodiment.
Figure 11C:
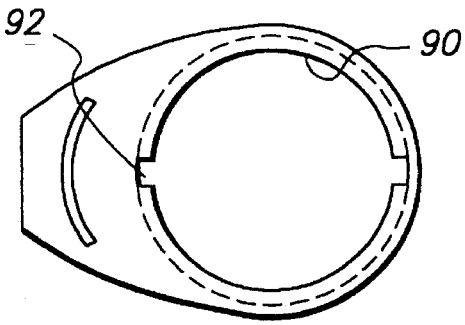
Figure 11D:
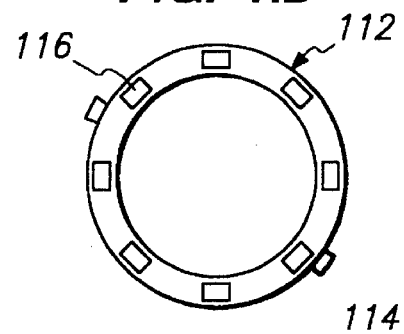
FIGS. 11D and 11E are top and side views respectively of a first desiccant overlay of the embodiment.
Figure 11F:
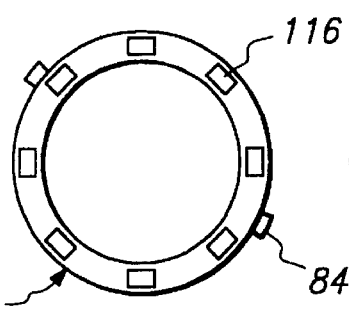
FIGS. 11F and 11G are top and side views respectively of a second desiccant overlay of the embodiment.
Figure 11H:
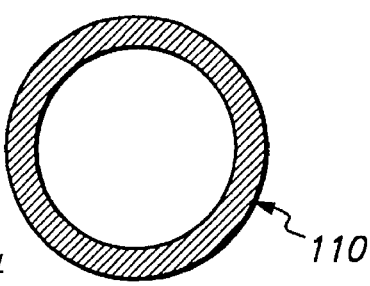
FIGS. 11H and 11I are top and side views respectively of the desiccant capsule of the embodiment.
Figure 11E:
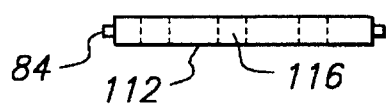
Figure 11G:
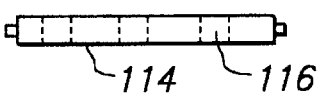
Figure 11I:
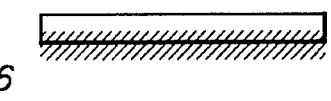
Figure 11J:
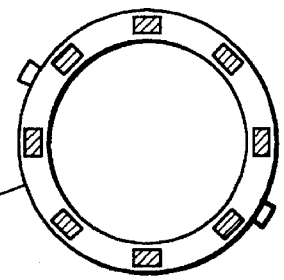
FIGS. 11J and 11K are top and side views of the desiccant assembly of the embodiment in operative condition.
Figure 11L:
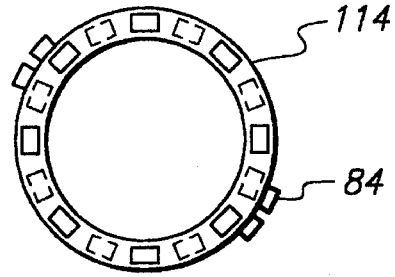
FIGS. 11L and 11M are top and side views respectively of the desiccant assembly of the embodiment in non-operative condition.
Figure 11K:
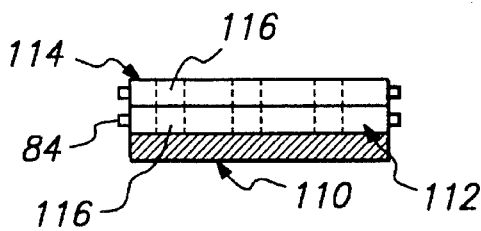
Figure 11M:
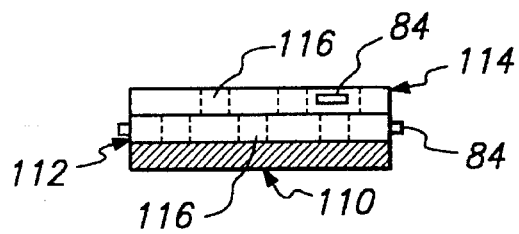
Figure 12A:
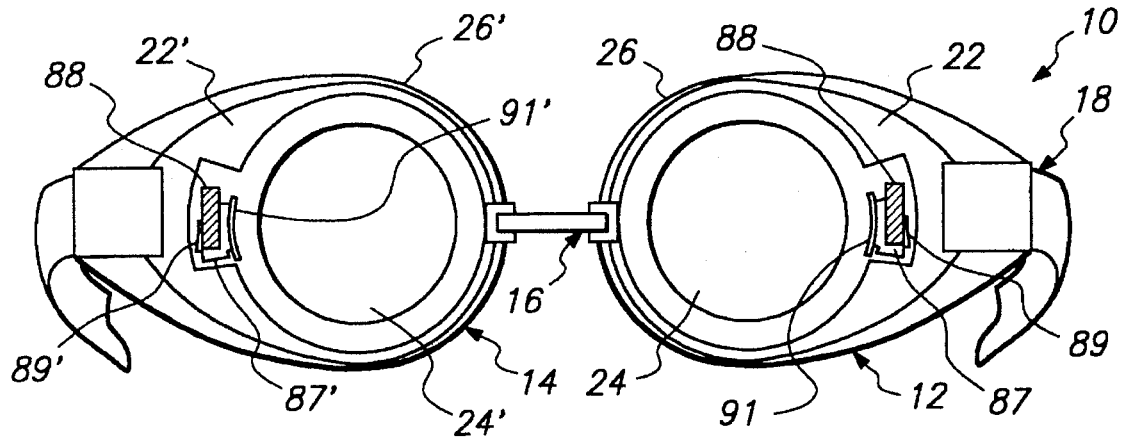
FIG. 12A is a frontal view of a eleventh embodiment of the assembly of the invention.
Figure 12B:
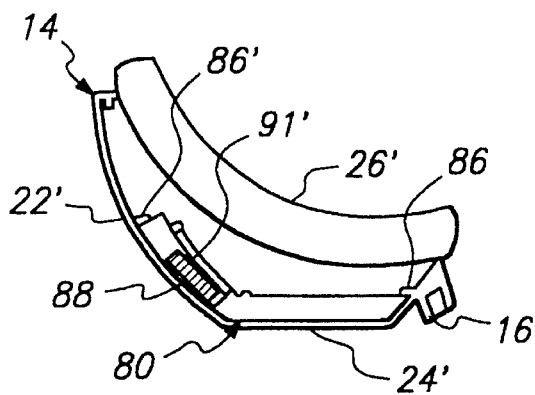
FIGS. 12B and 12C are side and top views respectively of the eye-cup of the embodiment.
Figure 12C:
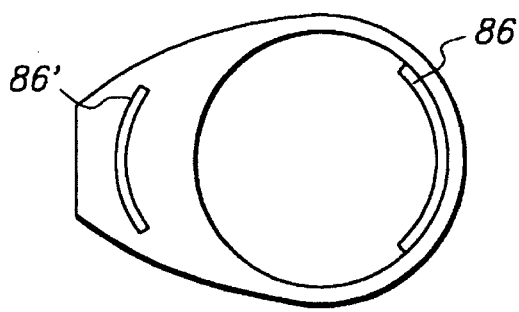
Figure 12D:
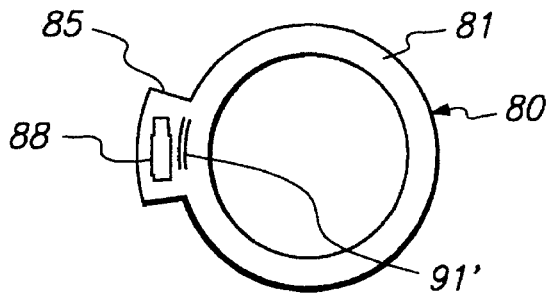
FIGS. 12D and 12E are top and side views respectively of the eye-cup shown in FIG. 12B.
Figure 12E:
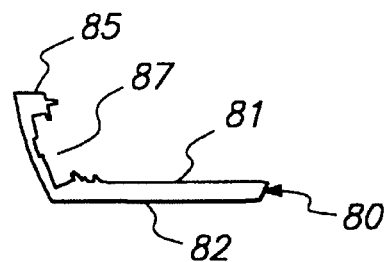
Figure 12F:
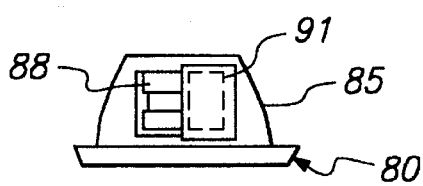
FIG. 12F is a view of the desiccant capsule inserted in operative configuration in the desiccant chamber of the eye-cup shown in FIG. 12B.
Figure 12G:
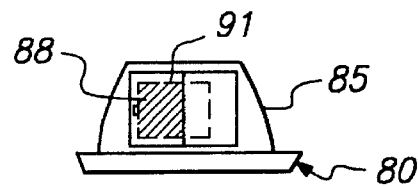
FIG. 12G is a view of the desiccant capsule inserted in non-operative configuration in the desiccant chamber of the eye-cup shown in FIG. 12B.
Figure 13A:
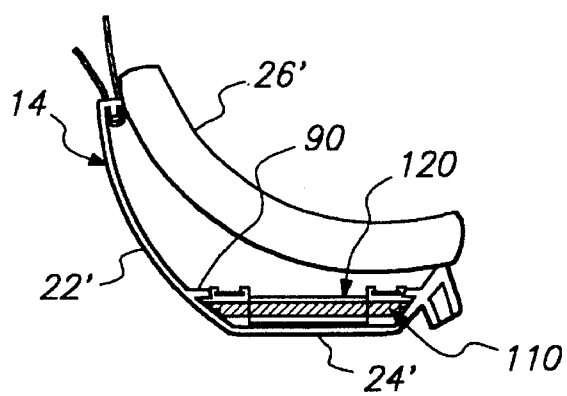
FIGS. 13A and 13B are side and top views of an eye-cup of a twelth embodiment of the invention.
Figure 13B:
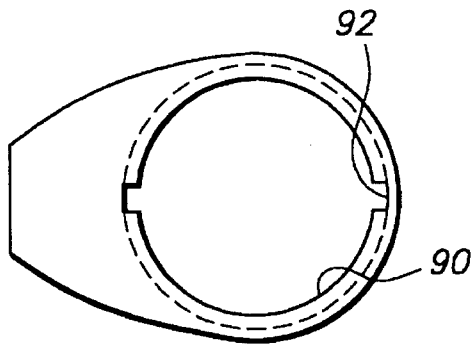
Figures 13C, 13E, 13G:
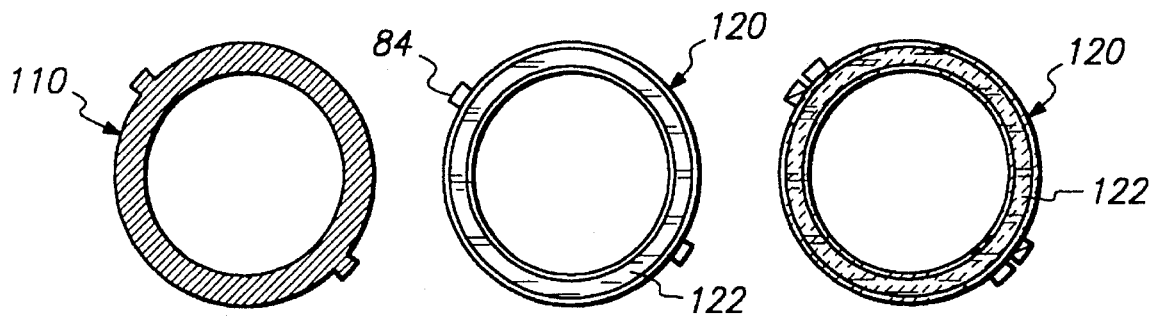
FIGS. 13C and 13D are top and side views respectively of the desiccant capsule of the embodiment.
FIGS. 13E and 13F are top and side views respectively of the desiccant capsule overlay of the embodiment.
FIGS. 13G and 13H are top and side views respectively of the desiccant assembly in operative configuration.
Figures 13D, 13F, 13H:
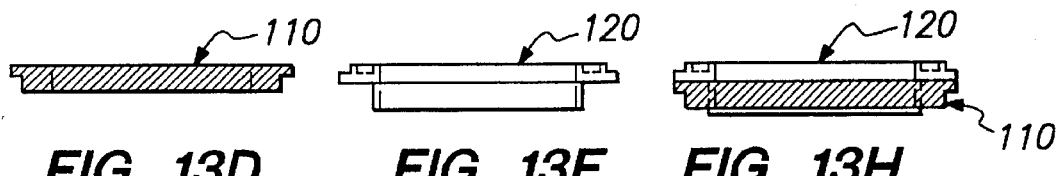
Figure 13I:
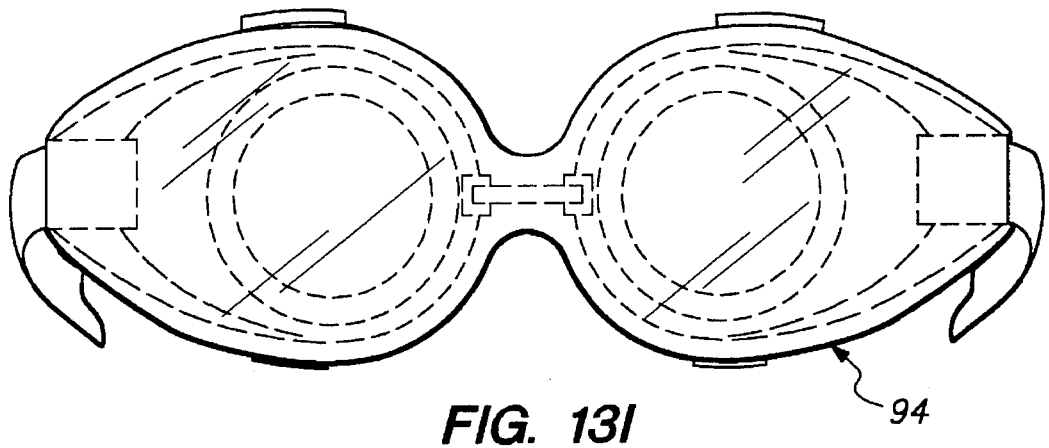
FIG. 13I is a front view of a form-fitting storage case for the assembly shown in FIG. 13A.
Figure 13J:
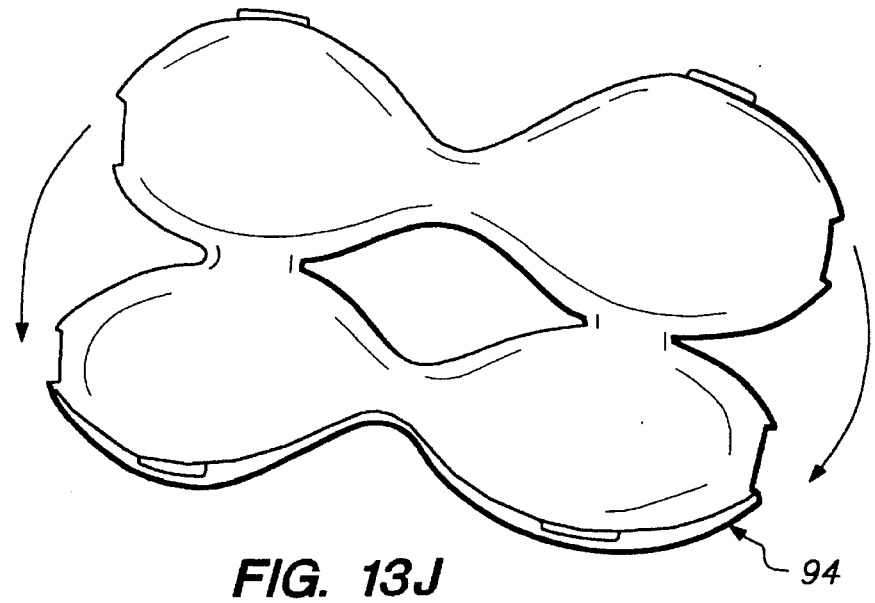
FIG. 13J is a view in perspective of the case shown in FIG. 13I in an open configuration.

In the first series of embodiments, the desiccant capsule takes the form of a desiccant ring 80, as shown in FIG. 5C. The ring is a flattened disc with an upper side 81 and a lower side 82. The upper side 81 of ring 80 is provided with a series of depressions 83, each capturing a solid mass of a desired desiccant 44. The edge of ring 80 is provided with two or more projections 84. The limb 22 of the eye-cup is provided with a capture rim 90, which forms the desiccant chamber, and is further provided with notches 92. Capture rim 90 is positioned at a distance from pane 24 sufficient to accommodate the thickness of ring 80, which is inserted into the desiccant chamber by aligning the projections of desiccant ring 80 with the notches 92 of capture rim 90, and thereafter pushing desiccant ring 80 into place.

Desiccant ring 80 can also be configured to provide an upward-projecting flange 85, as shown in FIGS. 6 and 7. Depending on the amount of desiccant 44 desired, both desiccant ring 80 and flange 85 can be provided with depressions 83 for holding desiccant 44, as shown in FIG. 6, or flange 85 only may be so configured, as shown in FIG. 7. In both instances, the nearly continuous extent of capture rim 90 that defines the desiccant chamber in FIG. 5, is not possible given the asymmetry provide by the flange. Rather, a pair of hinges 86 and 86' are provided to secure the ring-flange combination. Hinge 86 is positioned on the limb 22 at a sufficient distance from the pane to accommodate the thickness of the ring proper. Hinge 86' is positioned along limb 22 opposite the hinge 86, and at a distance sufficient to accommodate the thickness added to desiccant ring 80 by flange 85, as shown cross sectionally in FIGS. 6A and 7A.

Although desiccant ring 80 is designed for permanent retention of desiccant 44, flange 85 can be configured to provide a desiccant chamber 87 into which a desiccant capsule 88 can be reversibly inserted, utilizing prong 89. Alternatively, flange 85 can be configured for permanent capture of the desiccant. Because none of the desiccant capsules illustrated in FIGS. 5–7 can be sealed off from the atmosphere within goggle assembly 10, goggle assemblies incorporating such desiccant capsule embodiments include an air-tight case 94, such as those shown in FIG. 8, in order to preserve desiccant 44 when goggles assembly 10 is not being used.

As an alternative to a carrying case, flange 85 having a releasable desiccant capsule can be configured to provide its own desiccant sealing means, as shown in FIG. 12. In this embodiment, the flange is provide with a slidable door 91. When access to the desiccant is desired, the door can be moved to the open position, as shown in FIG. 12F. When the goggles are not in use and the user desires to preserve the desiccant, the door can be slid into a closed position, as shown in FIG. 12G.

FIG. 9 shows a sealable embodiment of the ring-shaped desiccant capsules discussed above. This embodiment is identical in all respects to the embodiment illustrated in FIG. 5 and described in detail above, except that a ring-shaped gate 100 is further included. The gate is provided with at least one aperture 102 that are positioned along the gate to match the positions of the desiccant in ring 80 as shown in the figures. Gate 100 is placed on the upper side 81 of ring 80, and the assembly thereafter inserted into place beneath rim 92 along the limb 22 of each eye-cup. It should be noted that gate 100 is freely rotatable beneath capture rim 90, allowing the user to align the apertures of the gate with the desiccant 44 of the ring in order to bring the desiccant in contact with air during goggles use. On the other hand, gate 100 can be rotated slightly to close off the desiccant 44 from the atmosphere when goggles assembly 10 is not being used.

FIG. 10 illustrates the same ring and gate assembly concept, except now as applied to the ring/flange combination just described and illustrated in FIGS. 6 and 7. As can be seen and appreciated from the figure, gate 100 is provided with a gate flange 103 similar in extent and position to flange 85 provided to desiccant ring 80. Gate flange 103 is positioned relative to the apertures 102 such that when the apertures are aligned with the desiccant 44 in the ring, gate flange 103 is displaced away from desiccant-containing flange 85 of ring 80, as shown in FIG. 10H. Once again, the desiccant of flange 85 can be configured for permanent retention, or may be configured provided with prongs for reversible insertion into the ring flange 85.

In a further embodiment, illustrated in FIG. 11, the desiccant is formed as solid, ring-shaped plug 110. Plug 110 is configured to fit within the eye-cup at its base against pane 24, along the inner edge of rim 22. The desiccant assembly is further provided with an inner ring gate 112 and an outer ring gate 114. Each of ring gates 112 and 114 is provided with at least one aperture 116. If more than one aperture is present, then they are aligned equidistant from one another around the periphery of the ring gates. The ring gates are further provided with projections 84, which are received by notches 92 of capture rim 90 of limb 22 of the eye-cup.

In operation, desiccant plug 110 is first inserted into the eye-cup, followed by the inner and outer ring gates 112 and 114. The sum of the widths of the desiccant plug and two ring gates is configured to be slightly less than the distance between capture rim 90 and the inner surface of pane 24. Examination of FIGS. 11J–11M will show that outer ring gate 114 can be rotated relative to inner ring gate 112 so as to align the apertures 116 of each gate and thereby expose desiccant plug 110. Alternatively, ring gates 112 and 114 can be rotated relative to one another in order to miss-align apertures 116, thereby sealing of desiccant plug 110 from contact with the atmosphere.

In yet another embodiment of the invention, as shown in FIG. 13, the desiccant can be formed as a solid, ring-shaped plug 110. The plug 110 could be inserted directly beneath the capture rim 90 formed along rim 22 of an eye-cup, or for added safety, could be partially encapsulated and held in place by a plug sleeve 120. Plug sleeve 120 is configured to capture desiccant plug 110 along its inner circumference and to cover the upper face of desiccant plug 110 such that the plug is secured within capture rim 90 and is not directly exposed within the eye-cup. Plug sleeve 120 is further provided with a circumferential water vapor permeable membrane 122. Water vapor permeable membrane 122 permits the passage of air and water vapor through plug sleeve 120 and into contact with desiccant plug 110, which absorbs the water vapor. as with several other embodiments, the desiccant plug of the present embodiment cannot be sealed off directly from the atmosphere. Rather this embodiment of the goggles assembly should be enclosed within an air-tight carrying case 94, such as those illustrated in FIG. 8.

Figure 14A:
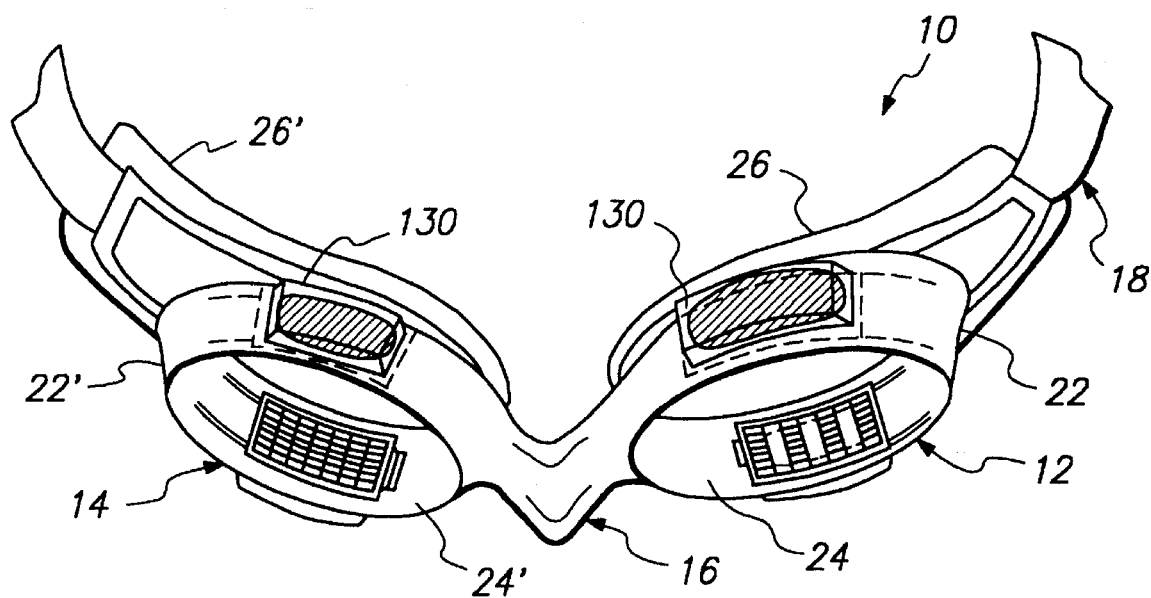
FIG. 14A is a view in perspective of a thirteenth embodiment of the assembly of the invention.
Figure 14B:
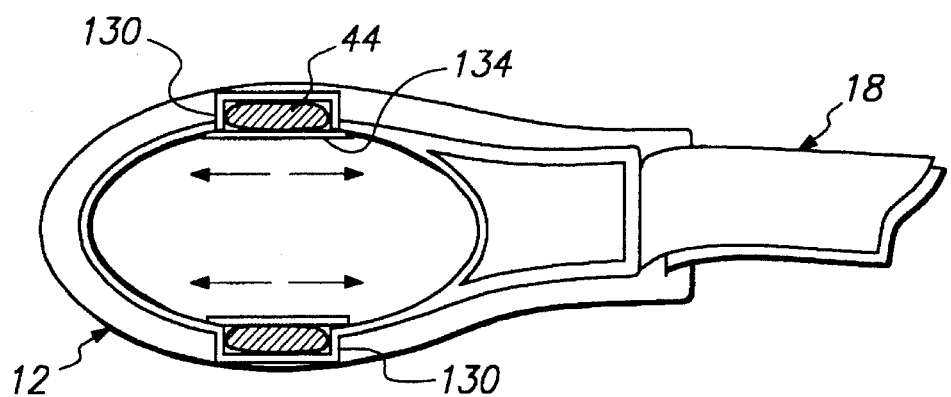
FIG. 14B is a top view of an eye-cup of the embodiment shown in FIG. 14A.
Figure 14C:
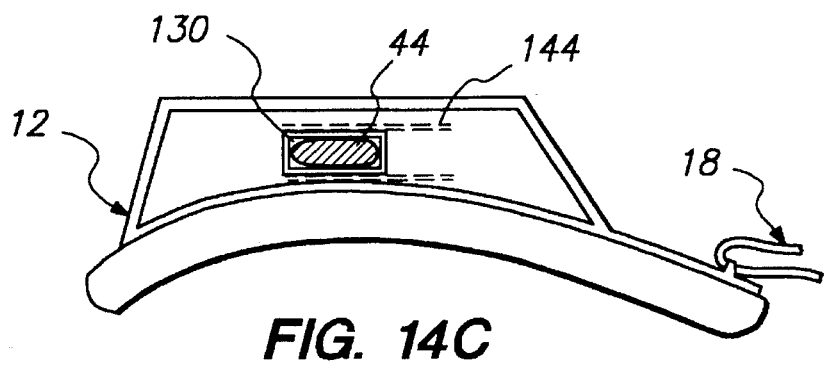
FIG. 14C is a side view of the eye-cup shown in FIG. 14B.
Figure 15B:
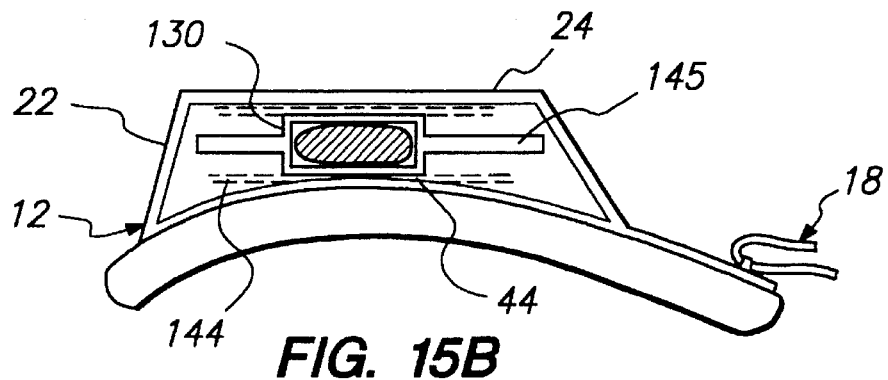
FIG. 15B is a top view of an eye-cup of the embodiment shown in FIG. 15A.
Figure 15C:
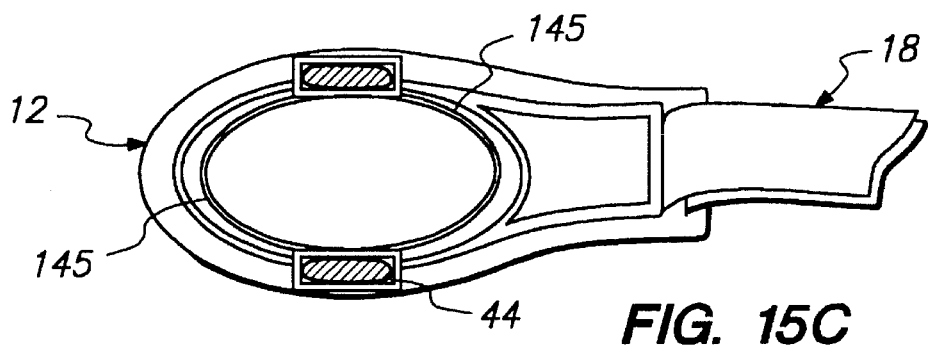
FIG. 15C is a front view of the eye-cup of shown in FIG. 15B.
Figure 15D:
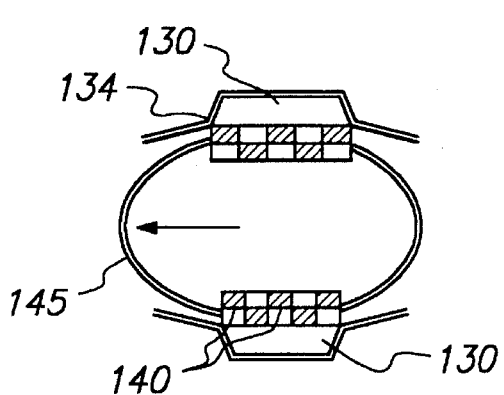
FIG. 15D is a partial cross sectional view of the eye cup of FIG. 15C showing the desiccant assemblies in non-operative configuration.
Figure 15F:
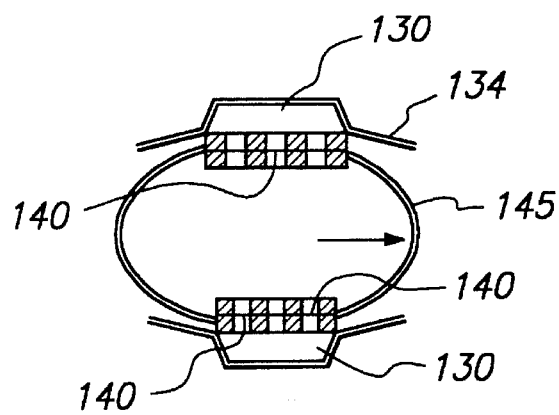
FIG. 15F is a partial cross sectional view of the eye cup of FIG. 15C showing the desiccant assemblies in operative configuration.
Figure 15E:
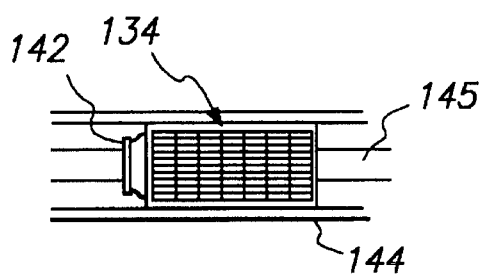
FIG. 15E is a top view of the gate of one of the desiccant assemblies of FIG. 15D in non-operative configuration.
Figure 15G:
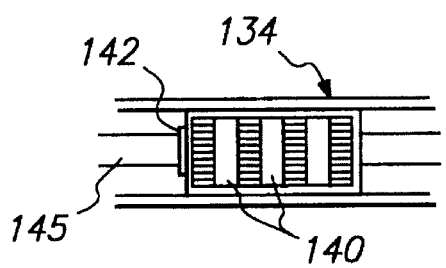
FIG. 15G is a top view of the gate of one of the desiccant assemblies of FIG. 15F in operative configuration.

FIG. 14 illustrates an embodiment utilizing disposable desiccant tablets or desiccant packets, such as those described in U.S. Pat. No. 3,990,872. In this embodiment, outward projecting desiccant chambers 130 are formed at one or more desired positions along rim 22 of an eye-cup. Desiccant chambers 130 open out on the interior surface of rim 22 through ports 132. Each of ports 132 is covered by a gate assembly 134 comprised of an outer panel 136 and an inner panel 138. The panels are each provided with at least one aperture 140 and are mounted one over the other so that the inner panel 138 can be slid relative to the outer panel 136 by pressing button 140. When button 140 is depressed, apertures 140 of the two panels line up to expose the desiccant to the air as in FIG. 14E. The apertures 140 of the two panels may also be mis-aligned to seal the dessicant off from the air, as in FIG. 14G. The gate assembly 134 is slidably mounted on gate tracks 144 formed along the inner surface of rim 22, making it possible to slide the gate assembly 134 back and expose the interior of desiccant chamber 130 so that a desired desiccant can be inserted and/or removed from the chamber.

It will be apparent from inspection of FIG. 14 that naked desiccant tablets of various sizes and shapes can both be inserted into and removed from desiccant chamber 130 when the gate assembly 134 is retracted. It will further be understood that a desiccant bag or capsule, such as those described in U.S. Pat. No. 3,990,872 are ideally suited for use in the desiccant chamber of the present embodiment.

Figure 19A:
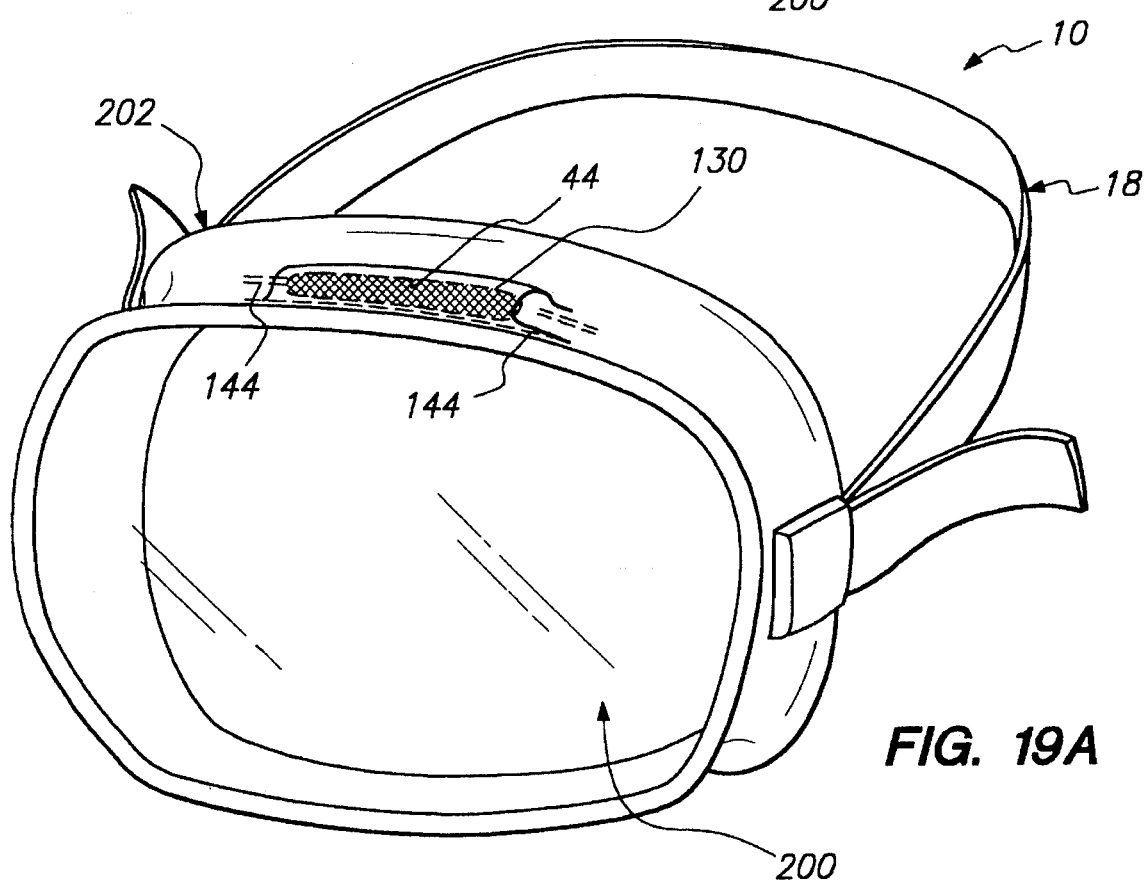
FIG. 19A is a view in perspective of a mask according to a seventeenth embodiment of the invention.
Figure 20C:
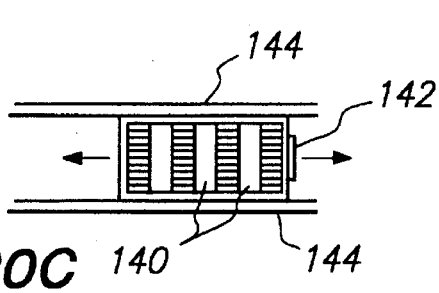
FIGS. 20C and 20D are top views of the gate of the desiccant assemblies shown in FIGS. 20A and 20B in operative and non-operative condition respectively.
Figure 20D:
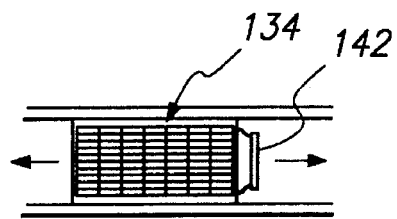
Figure 20E:
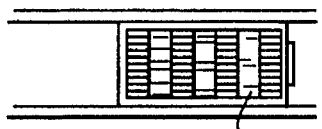
FIG. 20E is a top view of the gate shown in FIG. 20C further provided with a water vapor permeable screen.
Figure 20F:
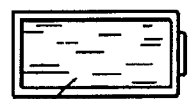
FIG. 20F is a top view of the water vapor permeable screen shown in FIG. 20E.
Figure 21A:
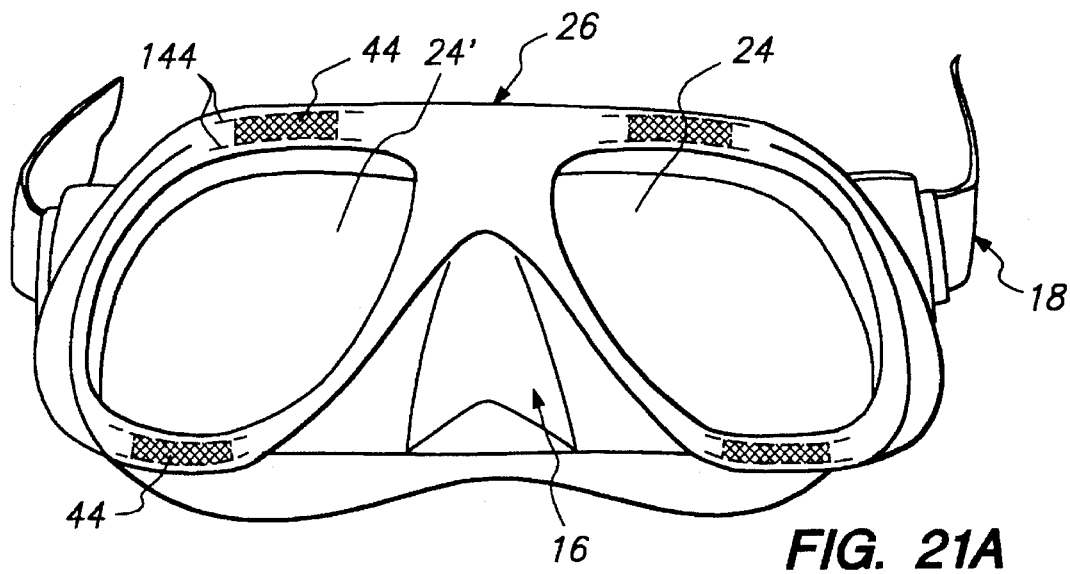
FIG. 21A is a view in perspective of a mask according to an nineteenth embodiment of the invention.
Figure 21B:
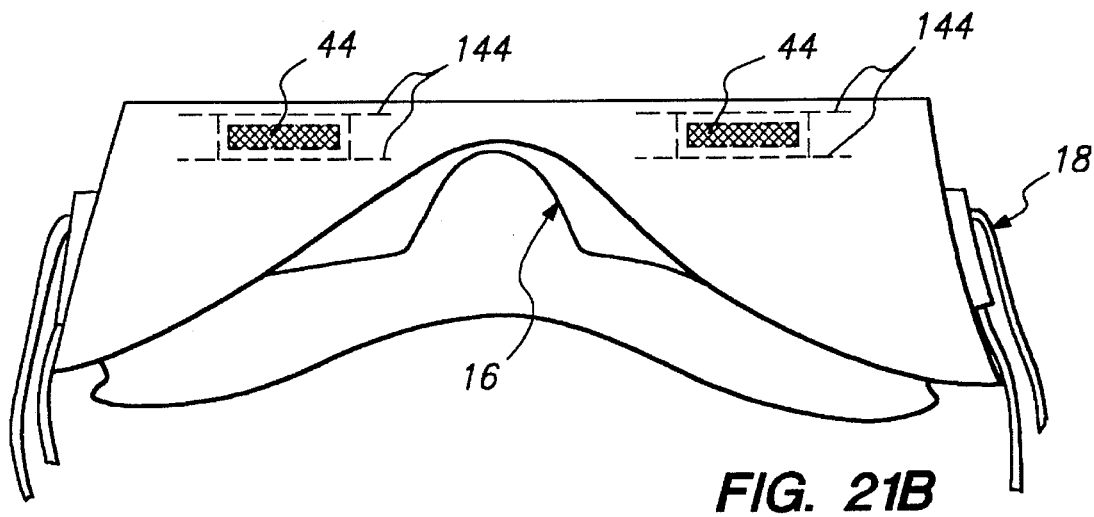
FIG. 21B is a top view of the mask shown in FIG. 21A.
Figure 21C:
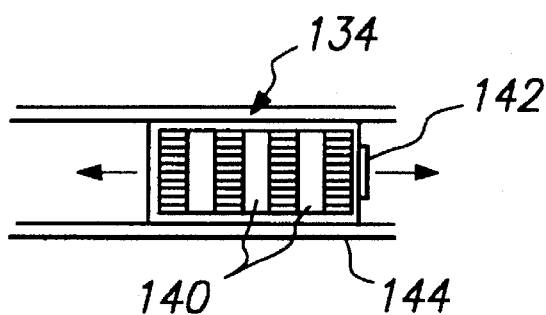
FIGS. 21C and 21D are top views of the gate of the desiccant assemblies shown in FIGS. 21A and 21B in operative and non-operative condition respectively.
Figure 21D:
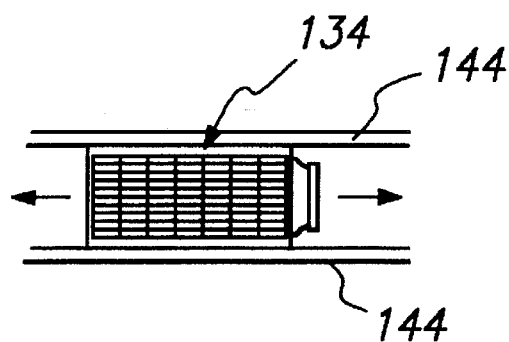
Figure 21E:
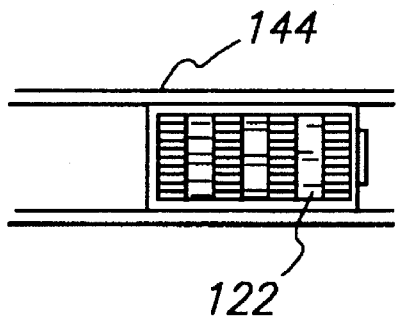
FIG. 21E is a top view of the gate shown in FIG. 21C further provided with a water vapor permeable screen.
Figure 21F:
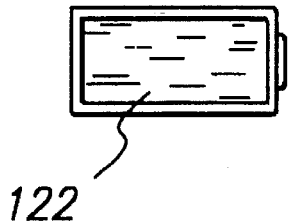
FIG. 21F is a top view of the water vapor permeable screen shown in FIG. 21E.

In a further variation on this embodiment, gate assembly 134 may be provided with a water vapor permeable means, such as a Tyvek® screen or similar membrane. Such a screen would be particularly preferable in instances where a naked desiccant tablet is desired and contact with liquid water therefore needs to be avoided. Alternatively, the gate assembly 134 can be omitted entirely, leaving only a slidable screen of the water vapor permeable 122. Of course in the case of an embodiment incorporating only a screen, such embodiment preferably includes an air-tight case for storing the goggles or mask when not in use. Mask-type embodiments analogous to the goggles embodiment just described and illustrated in FIG. 14 are shown in FIGS. 19–21.

As shown in FIG. 15, yet another embodiment of the goggles assembly 10 of the invention is disclosed. This embodiment is identical in most respects to the embodiment shown in FIG. 14, except that the outer panels 136 are connected by a continuous band 145 that interconnects the ends of the outer panels to one another. It will be appreciated from the figure that the gate assemblies 134 are positioned on gate tracks 144, and thus will slide away from and back over the desiccant chambers to permit desiccant loading and unloading of the chambers. However, the opening and closing of the gate assemblies 134 is accomplished by pressing bands 145. When bands 145 are pressed toward nose piece 16, the outer panels 136 slide across the inner panels 138 to align the apertures of the panels and expose the desiccant. Gate assembly 134 is closed by pressing bands 145 away from the nose piece, thereby miss-aligning the apertures of the panels and sealing off atmospheric contact with the desiccant.

A retrofit for existing non-desiccant goggles is illustrated in FIG. 16. The retrofit 150 comprises a desiccant capsule 152 and an attachment means, such as a track 154. The track 154 is glued or otherwise affixed at a desired position along rim 22 of each eye-cup. The desiccant capsule 152 is then coupled to the track, and the retrofit is complete. It should be noted that the desiccant capsule 152 can take many forms, but will generally comprise at least a housing 155 and a water vapor permeable membrane 156 within said housing to permit water vapor to contact and be absorbed by desiccant 44 within the housing. Further, the housing may be provided with a slidable door 158, that can be slid over and seal off the water vapor permeable membrane, in order to eliminate contact between the desiccant and the atmosphere when the goggles assembly is not in use.

In addition to swim and ski-goggles, diving and ski masks can be configured to utilize the desiccant concept of the invention. Exemplary diving and ski masks as shown in FIGS. 17–21 have a pane 200, a rim air tight seal 202 and a strap 204 is illustrated in FIG. 17. In this embodiment, the diving mask is provided with the retrofit 150 of the previous figure, affixed at a point along the rim seal 202 above, below or lateral to the line of site of the user. Other dessicant embodiments, such as those illustrated in FIGS. 5–16 are also possible with this mask configuration and the mask configurations illustrated in embodoments 18–21.

Turning now to the desiccants, dynamic and continuous drying agents that are relatively biologically inert are preferred. Further, such agents must have sufficient drying capacity to remove water vapor from the reservoir of air captured by the goggles or mask around the eyes and the skin of the face for at least several hours before needing recharge or replacement. Such desiccants include activated alumina (made from calcination of an alumina gel or aluminum oxide trihydrate into crystallized phases of transition aluminas), silica gel (made by dehydrating high-purity silica hydrosol) and molecular sieves (also called zeolites, crystalline framework aluminosilicates containing alkali metal cations) and clay desiccants. Further many of these desiccants, and in particular silica gel, can be impregnated with cobalt chloride that changes from blue to pink/red as the desiccant becomes saturated with water. Desiccants that can be fabricated as solids that are stable in the presence of liquid water may be utilized directly in the invention without resort to encapsulation. Powdered or granulated desiccants, or desiccants that tend to shatter in the presence of liquid water, should be encapsulated within a housing provided with a water vapor permeable membrane, such as the ones described above.

From the foregoing, it will be appreciated how the objects and features of the invention are met. The invention is significantly advantageous over the prior art in that it provides for the first time a mechanically efficient and effective means for preventing the fogging of interior ocular surfaces, a common and annoying problem encountered by the users of swim goggles, ski masks and similar athletic eye protector gear. The simple construction of the invention translates not only into significant production cost savings, thereby lowering cost to the consumer, but also makes possible the rapid retrofit of pre-existing goggles and masks currently in use. The invention is further advantageous in that the user need perform no maintenance other than the periodic replacement of the desiccant.

Although the invention has been described with respect to particular embodiments, it will be appreciated that various modifications of the apparatus and method are possible without departing from the invention, which is defined by the claims set forth below.

I claim:

1. A non-fogging, athletic goggles assembly suitable for swimming, diving, ski-ing or like athletic activities, said goggles assembly comprising:

a) goggles provided with air-sealing means for capturing a reservoir of air around a user's eyes; and b) desiccant means provided with a desiccant material for removing water vapor from the reservoir of air coupled to said goggles and in operative contact with the reservoir of air when said goggles assembly is in use, wherein water vapor present in the air reservoir passes into said desiccant means and is absorbed by the desiccant material, thereby preventing fogging of said goggles or mask assembly, and wherein said desiccant means further comprises attachment means for reversible coupling of said desiccant means to said goggles assembly.

2. A non-fogging, athletic goggles assembly suitable for swimming, diving, ski-ing or like athletic activities, said goggles assembly comprising:

a) goggles provided with air-sealing means for capturing a reservoir of air around a user's eyes; and b) desiccant means coupled to said goggles for removing water vapor from the reservoir of air, said desiccant means provided with a desiccant material and water vapor-permeable separating the desiccant material from the reservoir of air, wherein water vapor present in the air reservoir passes through the water vapor-permeable means into said desiccant means and is absorbed by the desiccant material, thereby preventing fogging of said goggles assembly, and wherein said desiccant means further comprises attachment means for reversible coupling of said desiccant means to said goggles assembly.

3. A non-fogging, athletic goggles assembly suitable for swimming, diving, ski-ing or like athletic activities, said goggles assembly comprising:

a) a first eye-cup having a first limb, a first air-sealing means coupled to the first limb for capturing a first reservoir of air around a user's first eye, at least one desiccant chamber formed on the first limb and a desiccant material captured within the desiccant chamber;

b) a second eye-cup having a second limb, a second air-sealing means coupled to the second limb for capturing a second reservoir of air around a user's second eye, at least one desiccant chamber formed on the second limb and a desiccant material captured within the desiccant chamber;

c) a nose piece interconnecting the first eye-cup and the second eye-cup, wherein water vapor present in the first and second air reservoirs passes respectively into the first and second desiccant chambers where the water vapor is absorbed by the desiccant material, thereby preventing fogging of said goggles assembly; and d) a first water vapor permeable means slidably mounted on the first limb of said first eye-cup and reversibly slidable over the first desiccant chamber; and a second water vapor permeable means slidably mounted on the second limb of said second eye-cup and reversibly slidable over the second desiccant chamber.

4. A non-fogging, athletic goggles assembly suitable for swimming, diving, ski-ing or like athletic activities, said goggles assembly comprising:

a) a first eye-cup having a first limb, a first air-sealing means coupled to the first limb for capturing a first reservoir of air around a user's first eye, and a first ring-shaped desiccant means provided with a desiccant material and received within the first limb;

b) a second eye-cup having a second limb, a second air-sealing means coupled to the second limb for capturing a second reservoir of air around a user's second eye, and second ring-shaped desiccant means provided with a desiccant material and received within the second limb; and c) a nose piece interconnecting the first eye-cup and the second eye-cup, wherein water vapor present in the first and second air reservoirs passes respectively into the first and second desiccant means and is absorbed by the desiccant material, thereby preventing fogging.

5. The goggle assembly of claim 4 wherein said first and second desiccant means further comprises attachment means for reversible coupling of said first and second desiccant rings to goggle assembly.

6. The goggle assembly of claim 5 further comprising a first and second water vapor permeable means received over the first and second desiccant rings and separating the rings from direct contact with the first and second air reservoirs.

* * * * *